(12) United States Patent
Griffin et al.

(10) Patent No.: US 6,297,250 B1
(45) Date of Patent: Oct. 2, 2001

(54) PYRIMIDOPYRIMIDINE COMPOUNDS

(75) Inventors: Roger J Griffin, Newcastle Upon Tyne; Nicola J Curtin, Tyne And Wear; Bernard T Golding, Newcastle upon Tyne; Alan H. Calvert, Tyne And Wear; David R. Newell, Northumberland, all of (GB)

(73) Assignee: Newcastle University Ventures Limited, Newcastle Upon Tyne (GB)

( * ) Notice: Subject to any disclaimer, the term of this patent is extended or adjusted under 35 U.S.C. 154(b) by 0 days.

(21) Appl. No.: 09/410,742

(22) Filed: Oct. 1, 1999

Related U.S. Application Data

(63) Continuation of application No. PCT/GB98/00966, filed on Apr. 1, 1998.

(30) Foreign Application Priority Data

Apr. 1, 1997 (GB) .................................................. 9706618

(51) Int. Cl.⁷ .......................... A61K 31/519; A01P 35/00; C07D 487/22
(52) U.S. Cl. ............................. 514/258; 544/256
(58) Field of Search ............................. 544/256; 514/257, 514/258

(56) References Cited

U.S. PATENT DOCUMENTS 4,963,541 * 10/1990 Brooks et al. ........................ 514/183

FOREIGN PATENT DOCUMENTS

| 105 447 | 4/1974 | (DD) . |
| 117 456 | 1/1976 | (DD) . |
| 11 16 676 | 11/1961 | (DE) . |

OTHER PUBLICATIONS

Chemical Abstracts, vol. 110, No. 1, 1989 Columbus, Ohio, US; abstract No. 185745c, Phillis, John: "Effect of 2 Nucleoside Transport Inhibitors, Diprydamole A. Soluflazine" p. 59; XP002073382see abstract & Brain Res., vol. 481, No. 2, 1989, pp. 309–316 USA.

Chemical Abstracts, Vo;. 101, No. 1, 1984 Columbus, Ohio, US; abstract No. 16967k,Nelson,J.: "Potentialisation of Methotrexate Toxycity by Dipyridamole." p. 37XP002073383 see abstract & Cancer Res. vol. 44, No.6, 1984, pp. 2493–2496, USA.

Dr.F.Eichholz: "Einfluss Von Pyrimidopyrimidin–U. Pteridin–Derivaten Auf Phosphat–U. Adenosin–Permeabilitat Menslicher Erythrocyten" Arzneimittel Forschung. Drug Research., vol. 15, No. 5, 1965, pp. 558–563,XP002073381 Aulendorf DE see p. 558—p. 563.

Chemical Abstracts, vol. 85, No. 28, 1976 Columbus, Ohio, US; abstract No. 108602s, p. 459 XP002073384 see abstract & Imai, Kazuo et al.: "Studies on the Synthesis of S–Containing Pyrimido (5,4–D) Pyrimidin Derivatives. II." Yakugaku Zasshi, vol. 96, No. 5, 1976, pp. 586–592, Tokyo.

Chemical Abstracts, vol. 87, No. 28, 1977 Columbus, Ohio, US; abstract No. 53351t, p.481;XP002073385 see abstract & JP 76 136 696 A ( OTSUKA PHARMA.) Nov. 26, 1976.

Chemical Abstract, vol. 87, No. 28, 1977 Columbus, Ohio, US; abstract No. 168081x, p. 583;PX002073386 see abstract & JP 07 759 190 A ( OTSUKA PHARMA.) May 16, 1977.

* cited by examiner

Primary Examiner—Richard L. Raymond
Assistant Examiner—Venkataraman Balasubramanian
(74) Attorney, Agent, or Firm—Pillsbury Winthrop LLP

(57) ABSTRACT

A range of dipyridamole analogues useful for inhibiting transport of nucleosides or purines across cell membranes, thereby to potentiate the activity of various cytotoxic antitumor drugs, is disclosed. These analogues comprise compounds having general structural formula (I) or pharmaceutically acceptable salts thereof; wherein $R_1$ is chloro and $R_3$ is diethanolamino, or $R_1$ and $R_3$ are identical and are selected from allyl, halo, diethanolamino, solketalo and a group having the formula: —O—$R_z$ or —NH$R_z$, $R_z$ being selected from alkyl, hydroxyalkyl, alkoxyalkyl, dialkoxyalkyl and 2-oxo-alkyl wherein the or each alkyl and/or alkoxy moiety has less than six carbon atoms, and $R_2$ and $R_4$ are identical and are selected from piperidino, N-tetrahydroisoquinolyl, and a benzylamino group having structural formula (II) wherein $R_5$ is H, or an optionally substituted alkyl or benzyl group, and $R_6$ and $R_7$ represent H or optional substituents in the aromatic nucleus selected from halo, alkyl, alkoxy, hydroxy, trifluoromethyl, azido, cyano, nitro, carboxyl, carboxylic ester, amino or a substituted amino $NR_xR_y$ where $R_x$ and $R_y$ each represent hydrogen or alkyl, subject to the provisos that (a) if $R_1$ and $R_3$ are both chloro or diethanolamino, $R_2$ and $R_4$ are not both benzylamino, i.e. $R_2$ and $R_4$ do not correspond to structure II with $R_5$, $R_6$ and $R_7$ each being hydrogen, and (b) if $R_2$ and $R_4$ are both piperidino, $R_1$ and $R_3$ are not both chloro, diethanolamino, solketalo or (2,3-dimethoxy)propoxy

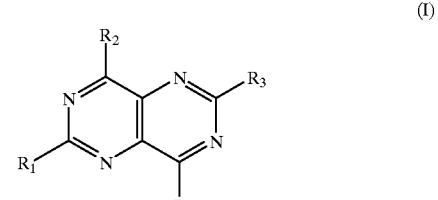

(I)

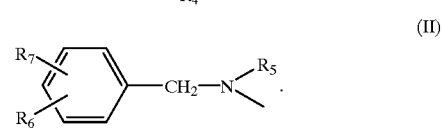

(II)

18 Claims, No Drawings

PYRIMIDOPYRIMIDINE COMPOUNDS

This application is a continuation of PCT/GB98/00966 filed on Apr. 1, 1998.

FIELD OF THE INVENTION

The present invention relates to dipyridamole analogues that are of interest as being potentially useful chemotherapeutic agents, especially insofar as they possess an ability to inhibit or modulate the transport of certain purine compounds and nucleosides across cell membranes of at least some cell types and are able thereby to enhance or potentiate the activity of certain cytotoxic drugs.

BACKGROUND

The compound 2,6-bis(diethanolamino)-4,8-dipiperidinopyrimidopyrimidine, known as dipyridamole and referred to as such in the present specification, and some particular close analogues thereof have been known for some considerable time as effective vasodilator and thrombolytic agents, as disclosed for example in patent documents GB799177 and GB807826 which also describe various methods of synthesis of such compounds. Although the pharmacological activity of dipyridamole is diverse, in at least most cases it is believed to arise as a result of its ability to inhibit or modulate the transport of nucleosides across cell membranes, this nucleoside transport being a major factor which is often implicated in the development of antitumor drug resistance. Not only can dipyridamole directly modulate the activity of cytotoxic compounds which are themselves nucleosides, e.g. cytarabine, fluordeoxyuridine and deoxycoformycin, or which are bases that become converted within the cell into nucleosides, e.g. fluorouracil, but dipyridamole can also indirectly modulate the activity of antimetabolites whose cytotoxicity is influenced by levels of normal nucleosides (e.g. methotrexate, the thymidylate synthase inhibitor CB3717, acivicin and PALA). In addition it is also known that dipyridamole can act to increase in vitro cytotoxicity of drugs such as doxrubicin, vinblastine and etoposide. The mechanism of action in the case of the latter cytotoxic compounds appears to involve the induction of higher intracellular drug levels, and it is believed that this may be caused, in part, by dipyridamole inhibiting drug efflux.

These properties of dipyridamole have led to proposals for using it in therapy, especially antitumor therapy, in combination with a range of cytotoxic drugs so as to enhance or potentiate the cytotoxicity of the latter. However, although a high level of activity in enhancing or potentiating the cytotoxicity of such drugs has been demonstrated in some cases in the course of in vitro experiments, clinical testing and use of dipyridamole in this manner, i.e. in combination with cytotoxic drugs, has been severely handicapped by a problem of low solubility and difficulty in satisfactory formulation for effective administration, together with a major problem arising from the fact that dipyridamole has a strong binding affinity to a plasma protein, $\alpha$-1 acid glycoprotein (AGP). This AGP protein is often present at elevated levels in cancer patients, and the effect of the strong AGP binding affinity of dipyridamole is to reduce the plasma or serum concentration of free dipyridamole. This in turn then reduces the ability of the dipyridamole to potentiate the activity of the drugs concerned since it seems that only free dipyridamole is able to modulate or inhibit the membrane transport of nucleosides and cytotoxic drugs.

DISCLOSURE OF THE INVENTION

One object of the present invention is accordingly to provide pyrimidopyrimidine compounds which can be regarded as being analogues or derivatives of dipyridamole and which, as compared with dipyridamole itself, have a reduced tendency to bind to AGP without any serious loss in ability to modulate or inhibit nucleoside transport across membranes of at least some cell types. A further object is to provide dipyridamole analogues or derivatives for therapeutic use which have a greater solubility in aqueous media, particularly at physiological pH, than dipyridamole itself.

It is also an object of the invention to provide a greater range of dipyridamole analogues or derivatives, which may constitute new chemical entities and/or new therapeutic agents, for increasing the choice available of potentially useful alternatives to dipyridamole itself for administering to patients in conjunction with certain cytotoxic drugs in order to potentiate the cytotoxic effectiveness of the latter.

A yet further object is to provide novel compounds that may be useful as intermediates in the preparation of bioactive dipyridamole analogues or derivatives as specified above for use as therapeutic agents.

Although many dipyridamole analogues or derivatives investigated are not necessarily significantly better than dipyridamole itself in respect of the properties that give rise to the problems mentioned above, certain analogue compounds have now been identified that it is believed will provide useful and viable alternatives to dipyridamole for use as therapeutic agents in chemotherapy. Moreover there are some compounds which not only exhibit a high degree of nucleoside transport inhibiting activity, comparable with or even stronger than dipyridamole itself, but which surprisingly also have a much reduced binding affinity for AGP as compared to dipyridamole whereby significant nucleoside transport inhibiting activity is retained in the presence of AGP, at least in respect of certain cell types. These compounds are accordingly of particular interest as therapeutic agents for use in medicine, especially when administered in conjunction with certain cytotoxic drugs, e.g. antitumor drugs, for increasing the cytotoxic effectiveness of the latter as previously mentioned.

The desirability of developing or identifying further dipyridamole analogues or derivatives for therapeutic use is also emphasised by recent work that has shown dipyridamole can act as an effective inhibitor of hypoxanthine uptake in selected tumour cell lines indicating that dipyridamole and like compounds have a potential for blocking hypoxanthine rescue based on uptake of extracellular purines such as hypoxanthine to counteract the cytotoxic effect of certain antifolate drugs such as liometerxol which normally act by inhibiting de navo purine biosynthesis within target cells. Further information and data about this aspect, and about other bioactive effects including effects relating to a potential for combating multidrug resistance, are presented in a paper by R. N. Turner, G. W. Aherne and N. J. Curtin entitled "Selective potentiation of lometerxol growth inhibition by dipyridamole through cell-specific inhibition of hyposanthine salvage", *Brit. Journal of Cancer* (1997), 76 (10), 1300–1307, and in reports by P. G. Smith et al "The potentiation of the multi-targeted antifolate (LY231514: MTA) by dipyridamole), *Proc. Amer. Assoc. Cancer Res.* (1998), 39, 2936 and by E. Marshman et al "Dipyridamole selectivity potentiates antipurine antifolates in human tumour cell lines but not normal tissue targets of dose-limiting toxicity", *Proc. Amer. Assoc. Cancer Res.* (1998), 39, 4143, the contents of which are incorporated herein by reference.

More specifically, from one aspect, the present invention provides pyrimidopyrimidine compounds constituting dipyridamole analogues for use in therapy as agents for modulating or inhibiting transport of nucleosides or purines across cell membranes, said compounds being compounds having the general structural formula I

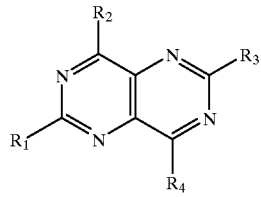

or pharmaceutically acceptable salts thereof, characterised in that in structural formula I $R_1$ is chloro and $R_3$ is diethanolamino, or $R_1$ and $R_3$ are identical and are selected from allyl, halo, diethanolamino, solketalo and a group having the formula —O—$R_Z$ or —NHR$_z$, $R_Z$ being selected from alkyl, hydroxyalkyl, alkoxyalkyl, dialkoxyalkyl and 2-oxo-alkyl wherein the or each alkyl and/or alkoxy moiety has less than six carbon atoms, and $R_2$ and $R_4$ are identical and are selected from piperidino, N-tetrahydroisoquinolyl, and a benzylamino group having the structural formula II

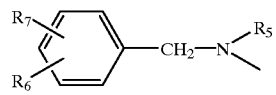

where $R_5$ is H, or an optionally substituted alkyl or benzyl group, and $R_6$ and $R_7$ represent H or optional substituents in the aromatic nucleus selected from halo, alkyl, alkoxy, hydroxy, trifluoromethyl, azido, cyano, nitro, carboxyl, carboxylic ester, amino or a substituted amino $NR_xR_y$ where $R_x$ and $R_y$ each represent hydrogen or alkyl, subject to the provisos that (a) if $R_1$ and $R_3$ are both chloro or diethanolamino, $R_2$ and $R_4$ are not both benzylamino, i.e. $R_2$ and $R_4$ do not correspond to structure II with $R_5$, $R_6$ and $R_7$ each being hydrogen, and (b) if $R_2$ and $R_4$ are both piperidino, $R_1$ and $R_3$ are not both chloro, diethanolamino, solketalo or (2,3-dimethoxy)propoxy.

From another aspect, the invention also resides in the use of a pyrimidopyrimidine compound as herein defined for the manufacture of a medical preparation for use in therapy for inhibiting membrane nucleoside or purine transport, such transport inhibition constituting an element of a therapeutic treatment, said compound providing the active transport inhibiting agent and being a pyrimidopyrimidine having the general formula I

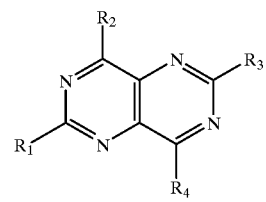

or a pharmaceutically acceptable salt and/or prodrug form thereof, characterised in that in structural formula I $R_1$ is chloro and $R_3$ is diethanolamino, or $R_1$ and $R_3$ are identical and are selected from allyl, halo, diethanolamino, solketalo and a group having the formula —O—$R_Z$ or —NHR$_z$, $R_Z$ being selected from alkyl, hydroxyalkyl, alkoxyalkyl, dialkoxyalkyl and 2-oxo-alkyl wherein the or each alkyl and/or alkoxy moiety has less than six carbon atoms, and $R_2$ and $R_4$ are identical and are selected from piperidino, N-tetrahydroisoquinolyl, and a benzylamino group having the structural formula II

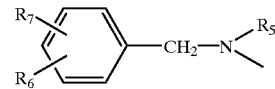

where $R_5$ is H, or an optionally substituted alkyl or benzyl group, and $R_6$ and $R_7$ represent H or optional substituents in the aromatic nucleus selected from halo, alkyl, alkoxy, hydroxy, trifluoromethyl, azido, cyano, nitro, carboxyl, carboxylic ester, amino or a substituted amino $NR_xR_y$ where $R_x$ and $R_y$ each represent hydrogen or alkyl, subject to the provisos that (a) if $R_1$ and $R_3$ are both chloro or diethanolamino, $R_2$ and $R_4$ are not both benzylamino, i.e. $R_2$ and $R_4$ do not correspond to structure II with $R_5$, $R_6$ and $R_7$ each being hydrogen, and (b) if $R_2$ and $R_4$ are both piperidino, $R_1$ and $R_3$ are not both chloro, diethanolamino, solketalo or (2,3-dimethoxy)propoxy.

The term solketalo is used herein to denote the group 2,2-dimethyl-1,3-dioxolane-4-methoxy.

When $R_1$ and/or $R_3$ is halo, this will preferably be chloro. Also, in preferred embodiments, when $R_2$ and $R_4$ are piperidino, $R_1$ and $R_3$ will be selected from allyl, methoxy, ethoxy, n-propoxy, iso-propoxy, iso-butoxy, 3-methylbutoxy, 2-oxo-n-propoxy, 2,2-diethoxy-n-propoxy, (2-methoxy-1-methyl)ethoxy, 2-methoxyethoxy, 2-hydroxypropoxy, 2-hydroxyethoxy and 3-hydroxypropoxy; when $R_2$ and $R_4$ are N-tetrahydroisoquinolyl, $R_1$ and $R_3$ will each be selected from diethanolamino and chloro; and when $R_2$ and $R_4$ are each a benzylamino group of structural formulae II, $R_1$ and $R_3$ will be selected from 2-methoxyethoxy, propoxy, 2-hydroxypropoxy, diethanolamino, solketalo, chloro, 2-hydroxyethoxy and 3-hydroxypropoxy.

In most of the preferred embodiments that are considered to be of greatest interest $R_2$ and $R_4$ are in fact each provided by a benzylamino group of formula II, and preferably at least one of $R_6$ and $R_7$ will be alkoxy, especially methoxy, which will most preferably be substituted in the 4-position but which can alternatively or additionally (in disubstituted derivatives) be substituted in the 3-position. When $R_5$ is alkyl, it is preferably methyl.

In general, all alkyl groups when present as such, or as a moiety in other groups such as alkoxy, will be lower alkyl groups composed of 1–6 carbon atoms, preferably 1–5 carbon atoms, and more usually 1–4 carbon atoms with $C_1$, $C_2$ and $C_3$ often being of particular interest.

In the development of this invention the dipyridamole analogue compounds prepared have been tested for their ability to modulate or inhibit nucleoside transport by measuring the percentage inhibition of thymidine uptake into L1210 cells growing in culture for a given concentration of compounds in the absence of, and in the presence of, the protein AGP.

The compounds of this invention that are of special interest possess significant nucleoside transport inhibitory activity which is largely retained in the presence of AGP, and as already indicated they thereby provide potentially very useful therapeutic agents for use in conjunction with other cytotoxic drugs, especially in connection with cancer chemotherapy. The compounds of this invention will generally have a lower AGP binding affinity than dipyridamole itself.

Within the series of dipyridamole analogue compounds in accordance with the invention wherein there are benzylamino groups conforming to structural formulae II, compounds of particular interest include compounds where the combination of substituents $R_5$, $R_6$ and $R_7$ is selected from the following combinations:

| $R_5$ | $R_6$ | $R_7$ |
| --- | --- | --- |
| H | 4-OMe | H |
| Me | 4-OMe | H |
| H | 4-OMe | 3-OMe |
| Me | 4-OMe | 3-OMe |
| H | H | H |
| Me | H | H |
| benzyl | H | H |
| H | 4-CF$_3$ | H |

Examples of specific compounds within this series that are of interest include
(A1) 2,6-di-(3-hydroxypropoxy)-4,8-di-(N-4-methoxybenzyl-N-methylamino)pyrimidopyrimidine
(A2) 2,6-bis-diethanolamino-4,8-di-(4-methoxybenzylamino)pyrimidopyrimidine
(A3) 2,6-bis-diethanolamino-4,8-bis-(3,4-dimethoxybenzylamino)pyrimidopyrimidine
(A4) 2,6-di-(2-hydroxypropoxy)-4,8-di-(4-methoxybenzylamino)pyrimidopyrimidine
(A5) 2,6-di(-3-hydroxypropoxy)-4,8-di(-4-methoxybenzylamino)pyrimidopyrimidine
(A6) 2,6-di-(2-hydroxyethoxy)-4,8-di-(N-4-methoxybenzyl-N-methylamino)pyrimidopyrimidine
(A7) 2-chloro-6-diethanolamino-4,8-bis[(3,4-dimethoxybenzyl)amino]pyrimidopyrimidine
(A8) 2,6-di(-3-hydroxypropoxy)-4,8-bis[(-3,4-dimethoxybenzyl)-N-methylamino]pyrimidopyrimidine
(A9) 2,6-bis(diethanolamino)-4,8-di(4-chlorobenzylamino)pyrimidopyrimidine
(A10) 2,6-di-(3-hydroxypropoxy)-4,8-di-(N-benzylmethylamino)pyrimidopyrimidine
(A11) 2,6-di(-2-hydroxyethoxy)-4,8-di(N-methylbenzylamino)pyrimidopyrimidine
(A12) 2,6-di(-2-methoxyethoxy)-4,8-dibenzylaminopyrimidopyrimidine
(A13) 2,6-di-(2-methoxyethoxy)-4,8-di-(N-benzyl-N-methylamino)pyrimidopyrimidine
(A14) 2,6-disolketalo-4,8-dibenzylaminopyrimidopyrimidine
(A15) 2,6-bis-diethanolamino-4,8-di-(4-trifluoromethylbenzylamino)pyrimidopyrimidine
(A16) 2,6-di(-2-methoxyethoxy)-4,8-bis(dibenzylamino pyrimidopyrimidine
(A17) 2,6-dipropoxy-4,8-di-(N-benzyl-N-methylamino)pyrimidopyrimidine
(A18) 2,6-di(-2-hydroxyethyl)amino-4,8-di(4-methoxybenzyl)aminopyrimidopyrimidine
(A19) 2,6-di(-2-hydroxyethylamino)-4,8-dibenzylaminopyrimidopyrimidine
(A20) 2,6-bis-diethanolamino-4,8-di-(N-methyl-N-[4-methoxybenzyl])aminopyrimidopyrimidine
(A21) 2,6-di-(2-hydroxyethyl)amino-4,8-bis-(3,4-dimethoxybenzyl)aminopyrimidopyrimidine
(A22) 2,6-Di-(3-hydroxypropoxy)-4,8-di-(N-[4-methoxybenzyl]-N-methyl)aminopyrimidopyrimidine
(A23) 2,6-Di-(2-hydroxyethoxy)-4,8-di-(N-benzyl-N-methyl)aminopyrimidopyrimidine It has been found that in this 4,8-dibenzylamino series of compounds, nucleoside transport inhibitory activity is usually enhanced by one or more alkoxy substituents, preferably methoxy substituents, and/or by N-methylation of the benzylamino group. Also, in this 4,8-dibenzylamino series at least one of $R_1$ and $R_3$ will usually be selected from diethanolamino, 2-hydroxypropoxy and 3-hydroxypropoxy in the most preferred compounds. When $R_2$ and $R_4$ are N-tetrahydroisoquinolyl, in a presently preferred embodiment $R_1$ and $R_3$ are both diethanolamino.

In the series of compounds in which $R_2$ and $R_4$ are provided by a piperidino group, compounds of particular interest include
(B1) (2-hydroxypropoxy)-4,8-dipiperidinopyrimidopyrimidine
(B2) (3-hydroxypropoxy)-4,8-dipiperidinopyrimidopyrimidine
(B3) (2-methoxyethoxy)-4,8-dipiperidinopyrimidopyrimidine
(B4) (2-hydroxyethoxy)-4,8-dipiperidinopyrimidopyrimidine
(B5) 2,6-bis[2,2-diethoxy]-n-propoxy-4,8-dipiperidinopyrimidopyrimidine
(B6) 2,6-di[2-oxo]-n-propoxy-4,8-dipiperidinopyrimidopyrimidine
(B7) 2,6-dimethoxy-4,8-dipiperidinopyrimidopyrimidine
(B8) 2,6-diethoxy-4,8-dipiperidinopyrimidopyrimidine
(B9) 2,6-di-3-methylbutoxy-4,8-dipiperidinopyrimidopyrimidine
(B10) (2-methoxy-1-methyl)ethoxy-4,8-dipiperidinopyrimidopyrimidine
(B11) 2,6-diallyl-4,8-dipiperidinopyrimidopyrimidine
(B12) 2,6-di-n-propoxy-4,8-dipiperidinopyrimidopyrimidine
(B13) 2,6-di-iso-propoxy-4,8-dipiperidinopyrimidopyrimidine
(B14) 2,6-di-iso-butoxy-4,8-dipiperidinopyrimidopyrimidine The invention also embraces or extends to methods of preparing compounds as hereinbefore defined (including intermediates in some cases), as well as to the therapeutic use of such compounds in treating mammals.

At least most of the dipyridamole analogue compounds of this invention can be prepared via 2,4,6,8- tetrachloropyrimidopyrimidine which is a key intermediate or precursor that can be reacted with selected amines and alcohols sequentially to replace the chloro substituents. In general, the chloro substituents in the 4 and 8 positions are more readily displaced by nucleophiles than the chloro substituents in the 2 and 6 positions so that, for example, an initial treatment of the tetrachloro compound with two equivalents of an amine followed by subsequent treatment with two equivalents of an alcohol can be used to obtain a stepwise replacement of the chloro substituents leading to the production of compounds with two different substituents located respectively in the 4,8 and the 2,6 positions. Further details will become apparent from numerous examples of the preparation of specific compounds hereinafter described.

As already indicated, the therapeutic use of the compounds of this invention includes their use for making medical or veterinary preparations or pharmaceutical formulations which will contain an effective nucleoside transport inhibiting amount of the active compound for administration to a patient in conjunction with a cytotoxic drug in order to increase the cytotoxic effectiveness of the latter. Such preparations or formulations may be made up in accordance with any of the methods well known in the art of pharmacy for administration in any suitable manner, for example orally, parenterally (including subcutaneously, intra-muscularly or intravenously), or topically, the mode of administration, type of preparations or formulation and the dosage being generally determined by the details of the associated cytotoxic drug chemotherapy that is to be enhanced or potentiated.

Accordingly, the invention also includes pharmaceutical compositions or preparations, conveniently in unit dosage form, for selective use in conjunction with cytotoxic drugs in antitumor therapy, said compositions or preparations comprising as an active nucleoside transport inhibitory substance a dipyridamole analogue compound as herein specified.

In making up such pharmaceutical formulations in the form of sterile liquid preparations for parental use for instance, a predetermined therapeutically effective non-toxic amount of the particular compound concerned may be dissolved in phosphate buffered- saline and the preparations may be presented in unit dosage form and contained in sealed ampoules ready for use. In general, at least in aqueous solution, concentrations not greater than 200 mg/ml will be preferred, but the amount and dosage routine required for optimum effectiveness will of course vary and is ultimately at the discretion of the medical or veterinary practitioner treating the mammal concerned in each particular case. In using the nucleoside transport inhibiting compounds of the present invention in conjunction with cytotoxic drugs, in some cases the compound and the cytotoxic drug may be administered sequentially, whilst in other cases they may be administered simultaneously. In the latter case, it may be possible for them conveniently to be incorporated in the same pharmaceutical formulation or composition.

As mentioned, the compounds according to this invention have at least a potential for use as nucleoside transport inhibitors, and in vitro tests hereinafter described have demonstrated positive pharmacological activity which is maintained even in the presence of AGP. It is believed that this reflects the activity to be found in vivo in the course of therapeutic clinical use.

It will be understood that many of the compounds in accordance with the invention which are herein referred to may be presented, when used as therapeutic agents, in the form of pharmaceutically acceptable salts, especially acid addition salts derived from an acid selected for example from the group comprising: hydrochloric, hydrobromic, sulphuric, nitric, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic.

It should also be understood that where reference is made in this specification to compounds of formula I in the context of their use as therapeutic agents such reference should be construed as extending not only to their pharmaceutically acceptable salts but also to other pharmaceutically acceptable bioprecursors (prodrug forms) where relevant. The term "prodrug" is used in the present specification to denote modified forms or derivatives of a pharmacologically active compound which biodegrade in vivo and become converted into said active compound after administration, especially oral or intravenenous administration, in the course of therapeutic treatment of a mammal. Such prodrugs are commonly chosen because of an enhanced solubility in aqueous media which helps to overcome formulation problems, and also in some cases to give a relatively slow or controlled release of the active agent.

A satisfactory prodrug must generally be a water-soluble derivative which is non-toxic and reasonably stable in solution at physiological pH but which will biodegrade or convert, e.g. by enzymatic degradation or by an enviromental pH change, to the active compound at the location required following administration in the course of therapy. For many of the compounds of the present invention, prodrug forms may be provided by carbamate or amino acid derivatives, e.g. glycine or other amino-acid carbamate derivatives, or by phosphate derivatives. Phosphate derivatives that are susceptible to enzymic dephosphorylation in vivo will often be preferred, especially water-soluble ammonium or alkali metal phosphate salts. These may be conveniently prepared in many cases from compounds of structural formula I having at least one hydroxyl group substituent amenable to phosphorylation by reacting for example with a dibenzyl phosphonate, preferably in the presence of a tertiary base such as N,N-diisopropylethylamine.

It should also be understood that where any of the compounds referred to can exist in more than one enantiomeric and/or diastereoisomeric form, all such forms, mixtures thereof, and their preparations and uses are within the scope of the invention.

DESCRIPTION OF EXAMPLES OF PREFERRED EMBODIMENTS

The following examples and description of stages in synthetic routes of preparation of various preferred compounds of interest serve to further illustrate the present invention, but should not be construed in any way as a limitation thereof. In many instances the compounds described are accompanied by an NU reference or identification code number.

First, in EXAMPLES 1A and 1B, the preparation is described of 2,4,6,8-tetrachloropyrimidopyrimidine and 2,6-Dichloro-4,8-dipiperidinopyrimidopyrimidine which are intermediates used in the preparation of many of the other dipyridamole analogues hereinafter described.

EXAMPLE 1A 2,4,6,8-Tetrachloropyrimidopyrimidine (NU3000)
(a) 1st Stage—Preparation of 1,5-Disodium 2,4,6,8-pyrimido[5,4-d]pyrimidine Tetrone Commercially available 2,4,6,8-pyrimido[5,4-d]-pyrimidine tetrone (4.9 g, 25 mmol) was added to a hot solution of 0.1M NaOH (500 ml) and the mixture was stirred with heating until boiling. Hot water (400 ml) was added until all the yellow powder dissolved, then the mixture was filtered under suction using hot filtration glassware. After cooling, the product crystallised from the filtrate and was filtered under reduced pressure and dried in vacuo ($P_2O_5$). The product was obtained as a bright yellow fluffy solid (6.15 g, 98%).

(b) 2nd Stage—Preparation of 2,4,6,8-Tetrachloropyrimidopyrimidine (NU3000)

To a solution of phosphorus pentachloride (15 g, 72 mmol) in phosphorus oxychloride (125 ml, 1.34mol) was added 1,S-Disodium 2,4,6,8-pyrimido[5,4-d]pyrimidine tetrone (3 g, 12.5 mmol). The mixture was heated under reflux for 20 hours at 140–150° C. Excess of phosphorus oxychloride was removed by distillation under vacuum and the brown residue deposited into crushed ice (60 g). The mixture was immediately filtered, and the resulting solid was washed with water and dried in vacuo ($P_2O_5$). This was extracted into chloroform (approximately 200 ml) using soxhlet apparatus, and the solvent was removed yielding the title compound as a yellow powder (1.07 g, 31%). $\delta_C$ ($CDCl_3$, 300 MHz) 141.91, 157.84, 165.78; m/z (EI) 268 ($M^+$, 80%), 236, 199, 173, 163, 111.

EXAMPLE 1B 2,6-Dichloro-4,8-dipiperidinopyrimidopyrimidine (NU3002)

Piperidine (0.8 ml, 8 mmol) was added to tetrachloropyrimidopyrimidine (0.54 g, 2 mmol) in THF (15 ml) and the resulting solution was stirred for 10 minutes until a yellow precipitate formed. Water (75 ml) was added and the mixture stirred for a further 10 minutes. The precipitate was filtered under suction, washed with water and dried in vacuo ($P_2O_5$) yielding the title compound as a yellow powder (0.62 g, 75%), m.p. 240–241° C., $\delta_H$ ($CDCl_3$, 200 MHz) 1.81 (12H, s, 2×$(CH_2)_3$), 4.15 (8H, s br, 2×$N(CH_2)_2$); m/z (EI) 366 ($M^+$–1), 198.

EXAMPLE 2

2,6-Di(n)propoxy-4,8-dipiperidinopyrimidopyrimidine (NU3064)

Sodium metal (0.24 g, 10.4 mmol) was added to propan-1-ol (6 ml) in dry THF (10 ml) and stirred until all had dissolved. The solvent was evaporated under a stream of $N_2$ and the residue was redissolved in dry THF (15 ml). 2,6-dichloro-4,8-dipiperidinopyrimidopyrimidine (0.367 g, 1 mmol) in dry THF (10 ml) was added to the alkoxide and the mixture heated under reflux for 16 hours. After cooling to room temperature water (20 ml) was added and the product extracted into ethyl acetate (3×40 ml). The organic layers were combined, dried ($MgSO_4$), filtered and the solvent removed in vacuo. Recrystallisation from methanol/water yielded the title compound as a white crystalline solid (0.173 g, 42%), m.p. 127–129° C. Found: C, 63.96; H, 8.36; N, 20.24. $C_{22}H_{34}N_6O_2$ requires C, 63.74; H, 8.27; N, 20.27%.

EXAMPLE 3

2,6-bis(2',2'-Diethylacetal-1-propoxy)-4,8-dipiperidinopyrimidopyrimidine (NU3065)

(a) 1st Stage—Preparation of Ethyl Pyruvate Diethyl Acetal

Ethyl pyruvate (22ml, 0.19 mmol) was dissolved in ethanol (30 ml) and to this was added triethyl orthoformate (35 ml) and p-toluenesulphonic acid (0.5 g) and the mixture stirred at 60° C. for 15 minutes. The temperature was slowly increased to 80° C. and the ethyl formate produced in the reaction distilled off After removal of all the ethyl formate (5 hours) the remaining mixture was neutralised with tri-ethanolamine (0.5 ml). Ethanol was removed in vacuo and the remaining liquor distilled under reduced pressure yielding the title compound as a clear colourless liquid (30.78 g, 61%), b.p. 80–83° C. at 15 mm Hg.

(b) 2nd Stage—Preparation of 2,2-Diethoxypropan-1-ol

Ethyl pyruvate diethyl acetal (5.0 g, 26.3 mmol) in anhydrous THF (10 ml) was added dropwise to a suspension of lithium aluminium hydride (1.0 g, 26.3 mmol) in anhydrous THF (40 ml) and the mixture was stirred for 15 minutes. Water (1 ml) was added followed by 2M sodium hydroxide (3 ml) then a further portion of water (1 ml). The grey suspension turned white and was filtered, washed with THF and the solvent removed in vacuo yielding a pale yellow oil which was purified by distillation under reduced pressure (0.75 g, 19%), b.p. 79–81° C. at 15 mm Hg.

(c) 3rd Stage—Preparation of 2,6-bis(2',2'-Diethylacetal-1-propoxy)-4,8-dipiperidinopyrimidopyrimidine Sodium metal (0.092 g, 4 mmol) was added to 2,2, diethylacetal propan-1-ol (0.592 g, 4 mmol) in dry THF (4 ml) and the mixture was stirred under nitrogen for 6 hours when all the sodium had dissolved. 2,6-dichloro-4,8-dipiperidinopyrimidopyrimidine (0.367 g, 1 mmol) in dry THF (10 ml) was added and the mixture heated under reflux for 48 hours. After cooling to room temperature, water (40 ml) was added and the crude product was extracted into ethyl acetate (4×40 ml). The combined extracts were dried ($MgSO_4$), filtered and the solvent removed in vacuo. Purification by column chromatography on silica gel, with petrol:ethyl acetate (5:1) as eluent then recrystallisation from petrol afforded the title compound as an off-white solid (0.197 g, 33%), m.p. 83–84° C. Found: C, 61.01; H, 8.45; N, 14.08. $C_3OH_{50}N_6O_6$ requires C, 60.99; H, 8.53; N, 14.23%.

EXAMPLE 4

2,6-Di(-2-oxopropoxy)-4,8-dipiperidinopyrimidopyrimidine (NU3066)

First, 2,6-bis(2',2'-diethylacetal-1-propoxy)-4,8-dipiperidinopyrimidopyrimidine (0.10 g, 0.17 mmol) was stirred in aqueous acetic acid (0.5 ml) at room temperature, and glacial acetic acid added until all had dissolved. The mixture was then stirred for 30 minutes. The solvent was removed by evaporation and the residue was further dried in vacuo. The title compound was recovered as a white solid (0.064 g, 85%), m.p. 188–189° C.

EXAMPLE 5

2,6-Dimethoxy-4,8-dipiperidinopyrimidopyrimidine (NU3067)

2,6-Di chloro-4,8-dipiperidinopyrimidopyrimidine (0.184 g, 0.5 mmol) was dissolved in dry THF (15 ml), then added to freshly prepared sodium methoxide (4.1 ml, 1.22M, 5 mmol) in dry THF (5 ml) under a $N_2$ atmosphere, and the mixture heated under reflux for 20 hours. After cooling to room temperature water (20 ml) was added and the product extracted into ethyl acetate (4×20 ml). The organic layers were combined, dried ($MgSO_4$), filtered and the solvent removed in vacuo. Recrystallisation from methanol/water yielded the title compound as a yellow crystalline solid (0.083 g, 46%), m.p. 130–131° C. Found: C, 59.41; H, 7.27; N, 22.17. $C_{18}H_{26}N_6O_2$ requires C, 60.32; H, 7.31; N, 23.44%.

EXAMPLE 6

2,6-Diethoxy-4,8-dipiperidinopyrimidopyrimidine (NU3068)

Sodium metal (0.115 g, 5 mmol) was added to ethanol (0.23 g, 5 mmol) in dry THF (5 ml) and stirred until all had dissolved. Then, 2,6-dichloro-4,8-dipiperidinopyrimidopyrimidine (0.184 g, 0.5 mmol) dissolved in dry THF (10 ml) was added to the alkoxide and the mixture was heated under reflux for 18 hours. After cooling to room temperature water (20 ml) was added and the product extracted into ethyl acetate (4×20 ml). The organic layers were combined, dried (MgSO$_4$), filtered and the solvent removed in vacuo. Recrystallisation from methanol/water yielded the title compound as an orange crystalline solid (0.167 g, 84%), m.p. 142–143° C. Found: C, 62.11; H, 7.81; N, 21.34. $C_{20}H_{30}N_6O_2$ requires C, 62.15; H, 7.82; N, 21.74%.

EXAMPLE 7

2,6-Di-iso-propoxy-4,8-dipiperidinopyrimidopyrimidine (NU3069)

Sodium metal (0.115 g, 5 mmol) was added to propan-2-1 (0.3 g, 5 mmol) in dry THF (5 ml) and stirred until all ad dissolved. 2,6-dichloro-4,8-dipiperidinopyrimidoyrimidine (0.184 g, 0.5 mmol) dissolved in dry THF (10 ml) was added to the alkoxide and the mixture heated under reflux for 96 hours. After cooling to room temperature water (20 ml) was added and the product extracted into ethyl acetate (4×20 ml). The organic layers were combined, dried (MgSO$_4$), filtered and the solvent removed in vacuo. Recrystallisation from methanol/water yielded the title compound as a yellow crystalline solid (0.24 g, 58%), m.p. 167–169° C. Found: C, 63.23; H, 8.32; N, 19.78. $C_{22}H_{34}N_6O_2$ requires C, 63.74; H, 8.27; N, 20.27%.

EXAMPLE 8

2,6-Di-(3'-methylbutoxy)-4,8-dipiperidinopyrimidopyrimidine (NU3070)

Sodium metal (0.115 g, 5 mmol) was added to 3-methylbutan-1-ol (0.44 g, 5 mmol) in dry THF (5 ml) and stirred until all had dissolved. 2,6-dichloro-4,8-dipiperidinopyrimidopyrimidine (0.184 g, 0.5 mmol) dissolved in dry THF (10 ml) was added to the alkoxide and the mixture heated under reflux for 72 hours. After cooling to room temperature, water (20 ml) was added and the product extracted into ethyl acetate (4×20 ml). The organic layers were combined, dried (MgSO$_4$), filtered and the solvent removed in vacuo. Recrystallisation from methanol/water yielded the title compound as a yellow crystalline solid (0.148 g, 63%), m.p. 105–106° C. Found: C, 66.73; H, 8.80; N, 17.48. $C_{26}H_{42}N_6O_2$ requires C, 66.35; H, 8.99; N, 17.86%.

EXAMPLE 9

2,6-Di-(2'-methylpropoxy)-4,8-dipiperidinopyrimidopyrimidine (NU3071)

Sodium metal (0.115 g, 5 mmol) was added to 2-methylpropan-1-ol (0.37 g, 5 mmol) in dry THF (5 ml) and stirred until all had dissolved. 2,6-dichloro-4,8-dipiperidinopyrimidopyrimidine (0.184 g, 0.5 mmol) dissolved in dry THF (10 ml) was added to the alkoxide and the mixture heated under reflux for 42 hours. After cooling to room temperature, water (20 ml) was added and the product extracted into ethyl acetate (4×20 ml). The organic layers were combined, dried (MgSO$_4$), filtered and the solvent removed in vacuo. Recrystallisation from methanol/water yielded the title compound as a yellow crystalline solid (0.122 g, 54%), m.p. 114–116° C.

EXAMPLE 10

2,6-Di-allyloxy-4,8-dipiperidinopyrimidopyrimidine (NU3072)

Sodium metal (0.115 g, 5 mmol) was added to allyl alcohol (0.291 g, 5 mmol) in dry THF (5 ml) and stirred until all had dissolved. 2,6-dichloro-4,8-dipiperidinopyrimidopyrimidine (0.184 g, 0.5 mmol) dissolved in dry THF (10 ml) was added to the alkoxide and the mixture heated under reflux for 72 hours. After cooling to room temperature, water (20 ml) was added and the product extracted into ethyl acetate (4×20 ml). The organic layers were combined, dried (MgSO$_4$), filtered and the solvent removed in vacuo. Recrystallisation from methanol/water yielded the title compound as a white crystalline solid (0.079 g, 40%), m.p. 109–110° C.

EXAMPLE 11

2,6-Di(1'-methoxy-2'-methyl)ethoxy-4,8-dipiperidinopyrimidopyrimidine (NU3074)

Sodium metal (0.115 g, 5 mmol) was added to 1-methoxy-2-propanol (0.45 g, 5 mmol) in dry THF (5 ml) and stirred until all had dissolved. 2,6-dichloro-4,8-piperidinopyrimidopyrimidine (0.184 g, 0.5 mmol) dissolved in dry THF (10 ml) was added to the alkoxide and the mixture heated under reflux for 72 hours. After cooling to room temperature, water (20 ml) was added and the product extracted into ethyl acetate (4×20 ml). The organic layers were combined, dried (MgSO$_4$), filtered and the solvent removed in vacuo. Purification by column chromatography on silica gel, with petrol:ethyl acetate (5:1) as eluent, gave the title compound as a cream coloured crystalline solid (0.053 g, 22%), m.p. 91–93° C. Found: C, 60.67; H, 7.94; N, 17.16 $C_{24}H_{38}N_6O_4$ requires C, 60.74; H, 8.07; N, 17.71%.

EXAMPLE 12

2,6-Di(2'-hydroxypropoxy)-4,8-dipiperidinopyrimidopyrimidine (NU3077)

(a) 1st Stage—Preparation of 2,6-Di[-2'-O-[(4"-methoxybenzyl)propoxy]-4,8-dipiperidinopyrimidopyrimidine Sodium metal (0.115 g, 5 mmol) was added to 2-O-(4-methoxybenzyl)propan-1-ol (0.98 g, 5 mmol) in dry THF (5 ml) and stirred at room temperature under nitrogen until all had dissolved. 2,6-dichloro-4,8-dipiperidinopyrimidopyrimidine (0.184 g, 0.5 mmol) in dry THF (10 ml) was added and the mixture heated under reflux for 48 hours. After cooling to room temperature water (20 ml) was added and the crude product extracted into ethyl acetate (4×15 ml). The organic layers were combined, dried (MgSO$_4$), filtered and solvent removed in vacuo yielding an orange mobile oil. Purification by column chromatography with petrol:ethyl acetate (6:1) and Hunig's Base (1.5%) as eluent afforded the title compound. m/z (EI) 686 (M$^+$, 2%).

(b) 2nd Stage—Preparation of 2,6-Di(2'-hydroxypropoxy)-4,8-dipiperidinopyrimidopyrimidine 2,6-Di[-2'-O-(4"-methoxybenzyl)propoxy]-4,8-dipiperidinopyridimidopyrimidine dissolved in methanol (40 ml) was stirred in an atmosphere of hydrogen in the presence a catalytic quantity of palladium/carbon for 4 hours. The mixture was filtered under reduced pressure through celite, washed with methanol and then the solvent was removed in vacuo. Purification by column chromatography with petrol:ethyl acetate (3:1) and Hunig's base (1%) as eluent afforded the title compound as a white crystalline solid (0.027 g, 10%), m.p. 128–129° C. Found: C, 59.31; H, 7.62; N, 18.24. $C_{22}H_{34}N_6O_4$ requires C, 59.17; H, 7.67; N, 18.82%.

EXAMPLE 13

2,6-Di(3'-hydroxypropoxy)-4,8-dipiperidinopyrimidopyrimidine (NU3085)

1,3-Propane diol (0.73 ml, 10 mmol) was dissolved in dry THF (10 ml), added to sodium hydride (0.24 g, 10 mmol) and the mixture was stirred at room temperature for 6 hours 2,6-dichloro-4,8-dipiperidinopyrimidopyrimidine (0.184 g, 0.5 mmol) in dry THF (25 ml) was added and the mixture heated under reflux 72 hours. After cooling to room temperature, water (30 ml) was added and the product extracted into ethyl acetate (4×20 ml). The organic layers were combined, dried ($MgSO_4$), filtered and solvent removed in vacuo. Purification was carried out by column chromatography on silica gel, with dichloromethane: methanol (95:5) as eluent. Subsequent recrystallisation from methanol/water gave the title compound as a cream solid (0.115 g, 51%), m.p. 154–156° C. Found: C, 59.23; H, 7.72; N, 18.79. $C_{22}H_{34}N_6O_4$ requires C, 59.17; H, 7.67; N, 18.82%.

EXAMPLE 14

2,6-Di(2'-hydroxyethoxy)-4,8-dipiperidinopyrimidopyrimidine (NU3086)

Ethylene glycol (0.56 ml, 10 mmol) was dissolved in dry THF (10 ml), then added to sodium hydride (0.24 g, 10 mmol) and stirred at room temperature for 6 hours. 2,6-dichloro-4,8-dipiperidinopyrimidopyrimidine (0.184 g, 0.5 mmol) in dry THF (25 ml) was added and the mixture heated under reflux for 96 hours. After cooling to room temperature, water (30 ml) was added and the product extracted into ethyl acetate (4×20 ml). The organic layers were combined, dried ($MgSO_4$), filtered and solvent removed in vacuo. Purification was carried out by column chromatography on silica gel, with dichloromethane: methanol (95:5) as eluent. This gave the title compound as an off-white solid (0.1 g, 45%), m.p. 148–150° C. Found: C, 57.54; H, 7.21; N, 19.41. $C_{20}H_{30}N_6O_4$ requires C, 57.40; H, 7.23; N, 20.08%.

EXAMPLE 15

2,6-Di(-2'-methoxyethoxy)-4,8-dipiperidinopyrimidopyrimidine (NU3093)

2-Methoxyethanol (0.38 g, 5 mmol) was dissolved in dry THF (5 ml) and added to sodium hydride (0.12 g, 5 mmol) and stirred for 8 hours at room temperature. 2,6-dichloro-4,8-dipiperidinopyrimidopyrimidine (0.184 g, 0.5 mmol) in dry THF (10 ml) was added to this and the mixture heated under reflux for 32 hours. After cooling to room temperature, water (30 ml) was added and the product extracted into ethyl acetate (4×20 ml), the organic layers combined, dried ($MgSO_4$), filtered and the solvent removed in vacuo. Recrystallisation from methanol/water yielded the title compound as a white solid (0.076 g, 34%), m.p. 127–128° C. Found C, 59.31; H, 7.60; N, 18.80. $C_{22}H_{34}N_6O_4$ requires C, 59.17; H, 7.67; N, 18.82%.

EXAMPLE 16A 2,6-Dichloro-4,8-di- (N-1,2,3,4-tetrahydroisoquinolyl)pyrimidopyrimidine (NU3075)

To a solution of 2,4,6,8-tetrachloropyrimidopyrimidine (0.54 g, 8.0 mmol) in THF (50 ml) was added a solution of 1,2,3,4-tetrahydroisoquinoline (1.0 ml) in THF (15 ml) dropwise over 10 minutes. The mixture was stirred for 12 hours at 25° C., the resultant solid was removed by filtration. The filtrate was evaporated under reduced pressure to afford a brown solid. Chromatography on silica gel, employing petrol:EtOAc (8:2) as eluent, afforded the title compound as a pale brown powder (0.27 g, 7%).

EXAMPLE 16B 2,6-bis-Diethanolamino-4,8-di-(N-1,2,3,4-tetrahydroisoquinolyl)pyrimidopyrimidine (NU3080) and 2-Chloro-6-diethanolamino-4,8-di-(N-1,2,3,4-tetrahydroisoquinolyl)pyrimidopyrimidine (NU3082)

A suspension of 2,6-dichloro-4,8-bis-(N-1,2,3,4-tetrahydroisoquinolyl)pyrimidopyrimidine (0.20 g, 0.4 mmol) in diethanolamine (5 ml) was stirred under nitrogen at 120° C. for 3 hours. After cooling, water (30 ml) was added and the reaction mixture was stood at 4° C. for 48 hours, whereupon a solid slowly deposited. The mixture was extracted with ethyl acetate (2×30 ml), and the combined organic layers were washed with water (30 ml), dried ($MgSO_4$) and evaporated in vacuo to afford a pale yellow solid. Chromatography on silica gel, utilising $CHCl_2$:MeOH (93:7) as eluent, afforded the title compound 2,6-bis-diethanolamino-4,8-di-(N-1,2,3,4-tetrahydroisoquinolyl)pyrimidopyrimidine (0.04 g, 17%). A second product recovered was identified as 2-chloro-6-diethanolamino-4,8-di-(N-1,2,3,4-tetrahydroisoquinolyl)pyrimidopyrimidine (0.04 g, 19%).

EXAMPLE 17

2,6-bis (Diethanolamino)-4,8-di[(4'-methoxybenzyl)amino]pyrimidopyrimidine (NU3076)

(a) 1st Stage—Preparation of 2,6-Dichloro-4,8-di[(4'-methoxybenzyl)amino]pyrimidopyrimidine 4-Methoxybenzylamine (0.27 ml, 2 mmol) was added to tetrachloropyrimidopyrimidine (0.135 g, 05 mmol) in THF (10 ml) and stirred for 10 minutes until a yellow precipitate formed. Water (40 ml) was added and the mixture stirred for a further 10 minutes. The precipitate was filtered under suction, washed with water and dried in vacuo ($P_2O_5$) yielding the title compound as a yellow powder (0.218 g, 93%), m.p. 186–188° C.

(b) 2nd Stage—Preparation of 2,6-bis (Diethanolamino)-4,8-di[(4'-methoxybenzyl)amino]pyrimidopyrimidine Diethanolamine (1 ml) was added to 2,6-dichloro-4,8-di[(4'-methoxybenzyl)amino]pyrimidopyrimidine (0.118 g, 0.25 mmol) and heated for 18 hours at 110° C. After cooling to room temperature water (40 ml) was added to give a precipitate which was filtered under reduced pressure. Recrystallisation of the crude material from methanol afforded the title compound as a yellow fluffy solid (0.047 g, 31%), m.p. 204–205° C. Found: C, 59.40; H, 6.37; N, 18.40. $C_{30}H_{40}N_8O_6$ requires C, 59.20; H, 6.37; N, 18.41%.

EXAMPLE 18

(R,R)-2,6-bis(2',2'-Dimethyl-1',3'-dioxolane-4'-methoxy)-4,8-dibenzylamino pyrimidopyrimidine (NU3078)

(a) 1st Stage—Preparation of 1,2;5,6-Di-O-isopropylidene-D-mannitol

Anhydrous zinc chloride (pre-dried over $P_2O_5$ in vacuo, 32 g, 0.235 mmol) was dissolved into freshly dried ($B_2O_3$) and distilled acetone (200 ml). The resulting solution was cooled to room temperature under anhydrous conditions. D-Mannitol (20 g, 0.11 mol) was added portionwise and the reaction mixture stirred at room temperature. After 24 hours a fresh solution of potassium carbonate (40 g) in water (40 ml) was added and stirred vigorously. The resulting precipitate was removed with portions of dichloromethane, the combined filtrate and washings were evaporated under reduced pressure to yield a white wet solid. This was dissolved in dichloromethane (100 ml) washed with water (100 ml), saturated $NaHCO_3$ (100 ml) then dried ($Na_2SO_4$), filtered and evaporated to give a white solid. Recrystallisation from n-hexane/ethyl acetate afforded the title compound as a white solid (9.23 g, 20%), m.p. 118–120° C.

(b) 2nd Stage - Preparation of 1,2-O-Isopropylidene-(S)-n-glycerol [Solketal (S)]

1,2:5,6-Di-O-isopropylidene-D-mannitol (5 g, 19 mmol) was added portionwise to a stirred solution of sodium periodate (5.97 g, 28 mmol) in water (75 ml), cooled in an ice bath. After 90 minutes, pre-cooled ethanol (110 ml) was added causing precipitation of a white solid. The solid was removed by filtration into a cooled flask. Sodium borohyride (1.5 g, 40 mmol) was added portionwise to the cooled filtrate. The mixture became viscous and a white precipitate formed which was stirred at room temperature for 2.5 hours. The precipitate was filtered and the filtrate reduced in vacuo (temp less than 25° C.) Distillation at water pump afforded the title compound as a clear colourless liquid (2.56 g, 99%).
(c) 3rd Stage—Preparation of 2,6-Dichloro-4,8-dibenzylaminopyrimidopyrimidine Benzylamine (0.22 ml, 2 mmol) was added to tetrachloropyrimidopyrimidine (0.135 g, 0.5 mmol) in THF (10 ml) and stirred for 10 minutes until a yellow precipitate formed. Water (40 ml) was added and the mixture stirred for a further 10 minutes. The precipitate was filtered under suction, washed with water and dried in vacuo ($P_2O_5$) yielding the title compound as a yellow powder (0.176 g, 86%), m.p. 229–230° C.
(d) 4th Stage—Preparation of (R,R)-2,6-bis(2',2'-Dimethyl-1',3'-dioxolane-4'-methoxy)-4,8-dibenzylamino pyrimidopyrimidine Sodium metal (0.115 g, 5 mmol) was added to (S) solketal (0.99 g, 7.5 mmol) in dry THF (10 ml) and stirred under reflux conditions for 48 hours. 2,6-dichloro-4,8-dibenzylaminopyrimidopyrimidine (0.103 g, 0.25 mmol) in dry THF (15 ml) was added and the mixture was heated under reflux for 54 hours. After cooling to room temperature water (20 ml) was added and the product was extracted into ethyl acetate (4×15 ml). The organic layers were combined, dried ($MgSO_4$), filtered and solvent removed in vacuo yielding the crude product as a yellow oil. Recrystallisation from petrol/ethyl acetate afforded the title compound as a cream solid (0.051 g, 34%), m.p. 113–115° C. Found C, 63.21; H, 6.21; N, 13.83. $C_{32}H_{38}N_6O_6$ requires C, 63.77; H, 6.36; N, 13.94%.

EXAMPLE 19

2,6-bis(Diethanolamino)-4,8-di[(4'-trifluoromethylbenzyl) amino]pyrimido pyrimidine (NU3079)
(a) 1st Stage—Preparation of 2,6-Dichloro-4,8-di[(4'-trifluoromethylbenzyl)amino]pyrimidopyrimidine 4-Trifluoromethylbenzylamine (0.28 ml, 2 mmol) was added to tetrachloropyrimidopyrimidine (0.135 g, 0.5 mmol) in THF (10 ml) and stirred for 10 minutes until a yellow precipitate formed. Water (40 ml) was added and the mixture stirred for a further 10 minutes. The precipitate was filtered under suction, washed with water and dried in vacuo ($P_2O_5$) yielding the title compound as an orange powder (0.28 g, 91%), m.p. 284–285° C.
(b) 2nd Stage—Preparation of 2,6-bis(Diethanolamino)-4,8-di[(4'-trifluoromethylbenzyl)amino]pyrimido pyrimidine Diethanolamine (1 ml) was added to 2,6-dichloro-4,8-di[(4'-trifluoromethylbenzyl)amino]pyrimidopyrimidine (0.136 g, 0.25 mmol) and heated for 18 hours at 110° C. After cooling to room temperature water (40 ml) was added giving a precipitate which was filtered under reduced pressure. Recrystallisation from dichloromethane afforded the title compound as a pale yellow solid (0.159 g. 93%), m.p. 194–196° C. Found: C, 52.57; H, 4.79; N, 15.90. $C_{30}H_{34}N_8O_4F_6$ requires C, 52.63; H, 4.73; N, 15.67%.

EXAMPLE 20

2-chloro-6-diethanolamino-4,8-bis[(3',4'-dimethoxybenzyl) amino]pyrimidopyrimidine (NU3081)

(a) 1st Stage—Preparation of 2,6-Dichloro-4,8-bis[(3',4'-dimethoxybenzyl)amino]pyrimidopyrimidine 3,4-Dimethoxybenzylamine (0.334 ml, 2 mmol) was added to tetrachloropyrimidopyrimidine (0.135 g, 0.5 mmol) in THF (10 ml) and stirred for 10 minutes until a yellow precipitate formed. Water (40 ml) was added and the mixture stirred for a further 10 minutes. The precipitate was filtered under suction, washed with water and dried in vacuo ($P_2O_5$) yielding the title compound as a yellow powder (0.221 g, 83%), m.p. 211–213° C.
(b) 2nd Stage—Preparation of 2-chloro-6-diethanolamino-4,8-bis[(3',4'-dimethoxybenzyl)amino]pyrimidopyrimidine Diethanolamine (1 ml) was added to 2,6-dichloro-4,8-di[(3',4'-dimethoxybenzyl)amino]pyrimidopyrimidine (0.118 g, 0.25 mmol) and heated for 18 hours at 110° C. After cooling to room temperature water (40 ml) was added giving a precipitate which was filtered under reduced pressure. Recrystallisation of the crude material from ethyl acetate/petrol afforded the title compound as a yellow fluffy solid (0.047 g, 31%), m.p. 101–103° C. Found: C, 55.69; H, 5.85; N, 16.66. $C_{28}H_{34}N_7O_6Cl$ required C, 56.04; H, 5.71; N, 16.34%.

EXAMPLE 21

2,6-bis(Diethanolamino)-4,8-di[(4'-chlorobenzyl)amino] pyrimido pyrimidine (NU3083)
(a) 1st Stage—Preparation of 2,6-dichloro-4,8-di[(4-chlorobenzyl)amino]pyrimidopyrimidine 4-Chlorobenzylamine (0.255 ml, 2 mmol) was added to tetrachloropyrimidopyrimidine (0.135 g, 0.5 mmol) in THF (10 ml) and stirred for 10 minutes until a yellow precipitate formed. Water (40 ml) was added and the mixture stirred for a further 10 minutes. The precipitate was filtered under suction, washed with water and dried in vacuo ($P_2O_5$) yielding the title compound as a yellow powder (0.162 g, 68%), m.p. 299–301° C.
(b) 2nd Stage—Preparation of 2,6-bis(Diethanolamino)-4, 8-di[(4'-chlorobenzyl)amino]pyrimido pyrimidine Diethanolamine (2 ml) was added to 2,6-dichloro-4,8-di [(4'-chlorobenzyl)amino]pyrimidopyrimidine (0.246 g, 0.5 mmol) and heated for 18 hours at 110° C. After cooling to room temperature water (40 ml) was added forming a precipitate which was filtered under reduced pressure. Filtration of the crude reaction mixture from hot ethyl acetate afforded the title compound as a yellow solid (0.16 g, 51%), m.p 223–224° C. Found: C, 54.45; H, 5.55; N, 18.01. $C_{28}H_{34}N_8O_4Cl_2$ requires C, 54.46; H. 5.55; N, 18.15%.

EXAMPLE 22

2,6-bis(Diethanolamino)-4,8-bis[(3',4'-dimethoxybenzyl) amino]pyrimidopyrimidine (NU3084)

Diethanolamine (5 ml) was added to 2,6-dichloro-4,8-di [3',4'-dimethoxybenzyl)amino]pyrimidopyrimidine (see Example 20) (0.266 g, 0.5 mmol) and heated for 72 hours at 110° C. After cooling to room temperature water (40 ml) was added forming a precipitate which was filtered under reduced pressure. Recrystallisation of the crude material from ethyl acetate afforded the title compound as a pale yellow solid (0.043 g, 13%), m.p. 176–179° C. Found: C, 57.20; H, 6.60; N, 16.62. $C_{32}H_{44}N_8O_8$ requires C, 57.47; H, 6.63; N, 16.76%.

EXAMPLE 23

2,6-Di(2'-hydroxypropoxy)-4,8-bis(4'-methoxybenzylamino)pyrimidopyrimidine (NU3087

Sodium hydride (0.48 g, 20 mmol) was added to 1,2-propanediol (1.46 ml, 20 mmol) in dry THF (10 ml) and stirred at 40° C. for 24 hours until all had dissolved. Then 2,6-dichloro-4,8-bis(4'-methoxybenzyiamino) pyrimidopyrimidine (see Example 17) (0.471 g, 1 mmol) in dry THF (30 ml) was added to the alkoxide and the mixture heated under reflux for 72 hours. After cooling to room temperature water (30 ml) was added and the product extracted with ethyl acetate (4×20 ml). The combined extracts were dried (MgSO$_4$) and the solvent evaporated. Chromatography on silica gel with dichloromethane:methanol (93:7) and then subsequent recrystallisation from iso-propanol yielded the title compound as a white solid (0.123 g, 22%), m.p. 190–192° C. Found C, 59.72; H, 6.06; N, 14.63. $C_{28}H_{34}N_6O_6$ requires C, 61.08; H, 6.22; N, 15.26.

EXAMPLE 24

2,6-Di(3'-hydroxypropoxy)-4,8-di[(N-benzylmethyl)amino]pyrimidopyrimidine (NU3088)

(a) 1st Stage—Preparation of 2,6-Dichloro-4,8-di[(N-benzylmethyl)amino]pyrimidopyrimidine N-Benzylmethylamine (0.242 g, 2 mmol) was added to tetrachloropyrimidopyrimidine (0.135 g, 0.5 mmol) in THF (10 ml) and stirred for 10 minutes until a yellow precipitate formed. Water (40 ml) was added and the mixture stirred for a further 10 minutes. The precipitate was filtered under suction, washed with water and dried in vacuo (P$_2$O$_5$) yielding the title compound as a yellow powder (0.159 g, 72%), m.p. 191–192° C.

(b) 2nd Stage - Preparation of 2,6-Di(3'-hydroxypropoxy)-4,8-di[(N-benzylmethyl)amino]pyrimidopyrimidine Sodium hydride (0.144 g, 6 mmol) was added to 1,2-propane diol (0.45 ml, 6 mmol) in dry THF (5 ml) and stirred for 10 hours at room temperature. To this was added 2,6-dichloro-4,8-di[(N-benzylmethyl)amino]pyrimidopyrimidine (0.132 g, 03 mmol) in dry THF (15 ml) and the resulting mixture was heated under reflux for 96 hours. After cooling to room temperature, water (30 ml) was added and the product extracted with ethyl acetate (4×20 ml). The combined extracts were dried (MgSO$_4$) and the solvent evaporated. Recrystallisation from methanol/water yielded the title compound as a cream fluffy solid (0.101 g, 65%), m.p. 109–111° C. Found: C, 64.78; H, 6.81; N, 16.16. $C_{28}H_{34}N_6O_4$ requires C, 64.85; H, 6.61; N, 16.20.

EXAMPLE 25

2,6-Di(2'-hydroxyethoxy)-4,8-di(4'-methoxybenzylamino)pyrimidopyrimidine (NU3089)

Sodium hydride (0.24 g, 10 mmol) was added to ethylene glycol (0.62 g, 10 mmol) in dry THF (5 ml) and stirred for 10 hours at room temperature. To this was added 2,6-Di(2'-hydroxyethoxy)-4,8-di(4'-methoxybenzylamino)pyrimidopyrimidine (see Example 17) (0.236 g, 0.5 mmol) in dry THF (15 ml) and the resulting mixture was heated under reflux for 72 hours. After cooling to room temperature water (30 ml) was added and the product extracted with ethyl acetate (4×20 ml). The combined extracts were dried (MgSO$_4$) and the solvent evaporated. Recrystallisation from iso-propanol yielded the title compound as an off-white powdery solid (0.048 g, 18%), m.p. 189–191° C. Found: C, 59.71; H, 5.72; N, 15.89. $C_{26}H_{30}N_6O_6$ requires C, 59.76; H, 5.79; N, 16.08.

EXAMPLE 26

2,6-Di(3'-hydroxypropoxy)-4,8-di[(N-4'-methoxybenzylmethyl)amino]pyrimidopyrimidine (NU3090)

(a) 1st Stage—Preparation of 2,6-Dichloro-4,8-di[(N-4-methoxybenzylmethyl)amino]pyrimidopyrimdine N-4-Methoxybenzylmethylamine (1.208 g, 8 mmol) was added to tetrachloropyrimidopyrimidine (0.54 g, 2 mmol) in THF (30 ml) and stirred for 10 minutes until a yellow precipitate formed. Water (80 ml) was added and the mixture stirred for a further 10 minutes. The precipitate was filtered under suction, washed with water and dried in vacuo (P2O5) yielding the title compound as a yellow powder (0.765 g, 77%), m.p. 172–174° C.

(b) 2nd Stage - Preparation of 2,6-Di(3'-hydroxypropoxy)-4,8-di[(N-4'-methoxybenzylmethyl)amino]-pyrimidopyrimidine Sodium hydride (0.096 g, 4 mmol) was added to 1,2-propane diol (0.304 ml, 4 mmol) in dry THF (5 ml) and stirred for 10 hours at room temperature. 2,6-dichloro-4,8-di[(N-4'-methoxybenzylmethyl)amino]pyrimidopyrimidine (0.20 g, 0.4 mmol) in dry THF (15 ml) was added and the resulting mixture was heated under reflux for 96 hours. After cooling to room temperature, water (30 ml) was added and the product extracted with ethyl acetate (4×20 ml). The combined extracts were dried (MgSO$_4$) and the solvent evaporated. Purification by column chromatography on silica gel with dichloromethane: methanol (95:5) as eluent and then recrystallisation from methanol/water yielded the title compound as a cream crystalline solid (0.044 g, 19%), m.p. 125–127° C. Found: C, 61.67; H, 6.54; N, 14.16. $C_{30}H_{38}N_6O_6$ requires C, 61.69; H. 6.66; N, 14.39.

EXAMPLE 27

2,6-Di(n)propoxy-4,8-di[(N-benzylmethyl)amino]-pyrimidopyrimidine (NU3091)

Propan-1-ol (0.30 g, 5 mmol) was dissolved in dry THF (5 ml) and added to sodium hydride (0.12 g, 5 mmol) and stirred for 9 hours at room temperature. 2,6-dichloro-4,8-di [(N-benzylmethyl)amino]pyrimidopyrimidine (see Example 24) (0.22 g, 0.5 mmol) in dry THE (10 ml) was added to this and the mixture heated under reflux for 48 hours. After cooling to room temperature, water (30 ml) was added and the product extracted into ethyl acetate (4×20 ml). The organic layers were combined, dried (MgSO$_4$), filtered and the solvent removed in vacuo. Recrystallisation from methanol/water yielded the title compound as white needles (0.103 g, 40%), m.p. 119–120° C. Found: C, 69.05; H, 6.75; N, 17.12. $C_{29}H_{34}N_6O_2$ requires C, 69.11; H, 7.04; N, 17.27%.

EXAMPLE 28

2,6-Di(-2'-methoxyethoxy)-4,8-di[(N-benzylmethyl)amino]-pyrimidopyrimidine (NU3092)

2-Methoxyethanol (0.38 g, 5 mmol) was dissolved in dry THF (5 ml). The resulting solution was added to sodium hydride (0.12, 5 mmol) and the mixture stirred for 9 hours at room temperature. 2,6-dichloro-4,8-di[(N-benzylmethyl)amino]pyrimidopyrimidine (0.22 g, 0.5 mmol) in dry THF (10 ml) was added and the mixture heated under reflux for 48 hours. After cooling to room temperature, water (30 ml) was added and the product extracted into ethyl acetate (4×20 ml). The organic layers were combined, dried (MgSO$_4$), filtered and the solvent removed in vacuo. Recrystallisation from methanol/water yielded the title compound as white needles (0.103 g, 40%), m.p. 116–118° C. Found: C, 64.89; H, 6.50; N, 16.24. $C_{28}H_{34}N_6O_4$ requires C, 64.85; H, 6.61; N, 16–20%.

EXAMPLE 29

2,6-Di-(2-hydroxyethylamino)-4,8-dibenzylaminopyrimidopyrimidine (NU3101)

(a) 1st Stage—Preparation of 4,8-dibenzylamino-2,6-dichloropyrimidopyrimidine

Benzylamine (1.00 ml, 9.26 mmol) was added to a solution of 2,4,6,8-tetrachloropyrimido-pyrimidine (0.50 g, 1.85 mmol) in dry THF (20 ml), containing $K_2CO_3$ (1.40 g, 13.89 mmol), under a $N_2$ atmosphere. The reaction mixture was stirred at room temperature for 20 min, water (30 ml) was added and stirring was continued for a further 20 min. The resultant precipitate was collected by filtration, washed with water, and dried in vacuo to yield the named product (0.53 g, 70%) as a pale yellow solid. NMR data was as follows:

$\delta_H$ (200 MHz, $CDCl_3$) 4.73–4.76 (d, 4H, 2×$ArCH_2NH$, J=6 Hz), 7.22–7.29 (t, 2H, 2×$ArCH_2NH$), 7.33(m, 1OH, 10×Ar-H); m/z (EI) 410, 412, 414 ($M^+$, 9:6:1 ratio, 31%), 270, 106, 91 (100%).

(b) 2nd Stage—Preparation of 2,6-Di-(2-hydroxyethylamino)-4,8-dibenzylaminopyrimidopyrimidine (NU3101)

A mixture of 2,6-dichloro-4,8-di-(benzylamino) pyrimidopyrimidine (0.32 g, 0.78 mmol) and ethanolamine (2 ml) was stirred at 150° C. for 12 h. The reaction mixture was cooled to room temperature and water (15 ml) was added, after which the mixture was stirred for a further 20 min, filtered, washed with water, and the collected solid dried in vacuo. Purification by silica column chromatography (dichloromethane: methanol, 9:1) yielded the title compound (0.11 g, 31%) as a fluorescent yellow solid (Found: C, 61.0; H, 6.0; N, 23.7. $C_{24}H_{28}N_8O_2.0.14CH_2Cl_2$ requires C, 61.4; H, 5.6; N, 23.2); NMR data was as follows:

$\nu_{MAX}$ ($KBr/cm^{-1}$) 3396, 3358, 3058, 2920, 747 and 715); $\delta_H$ (200 MHz, $d_6$-DMSO) 3.41–3.46 (m, 4H, 2×$NHCH_2CH_2OH$), 3.55–3.60(m, 4H, 2×$NHCH_2CH_2OH$), 4.65–4.68 (t, 2H, 2×OH, J=5 Hz), 4.72–4.76(d, 4H, 2×$PhCH_2$, J=6 Hz), 6.07–6.13 (t, 2H, 2×NH, J=6 Hz), 7.72–7.75 (t, 2H, 2×NH, J=6 Hz); m/z (EI) 460 ($M^+$, 18%), 416 ($M^+$—$CH_2CHO$), 91 ($C_7H_7^+$, 100%), 69 ($C_5H_9^+$); $\delta_C$ (200 MHz, $d_6$-DMSO) 43.42 ($HOCH_2CH_2NH$), 44.07 ($HOCH_2CH_2NH$), 60.64 ($PhCH_2NH$), 127.02 (Ar-C-2), 127.63 (Ar-C-3), 127.89 (Ar-C-4/8), 128.57 (Pyr C-5), 140.22 (Ar-C-1), 156.44 (Pyr C-5), 158.35 (Pyr C-2/6).

Similarly prepared from 2,6-dichloro-4,8-di(benzylamino)pyrimidopyrimidine or 2,6-dichloro-4,8-di-(N-methoxy-N-methylbenzylamino) pyrimidopyrimidine and either ethanolamine or diethanolamine were the following compounds:

EXAMPLE 30

2,6-Di-(2-hydroxyethyl)amino-4,8-di-[4-methoxybenzyl]-aminopyrimidopyrimidine (NU3099)

m.p. 161–163° C. (Found C, 59.14; H, 6.30; N, 21.61. $C_{26}H_{32}N_8O_4.0.25H_2O$ requires C, 59.47, H, 6.24, N, 21.34.

EXAMPLE 31

2,6-bis-Diethanolamino-4,8-di- (N-[4-methoxybenzyl]-N-methyl)aminopyrimidopyrimidine (NU3102)

m.p. 190–192° C. (Found C, 59.61; H, 6.99; N, 16.55. $C_{32}H_{44}O_6N_8$ 0.50EtOAc requires C, 59.14; H, 6.82; N, 17.24).

EXAMPLE 32

2,6-Di-(2-hydroxyethylamino)-4,8-di-[3,4-dimethoxybenzyl]aminopyrimidopyrimidine (NU3104)
NMR data was as follows:

$\delta_H$ (200 MHz, $d_6$-DMSO) 3.43–3.51 (t, 4H, 2×$NHCH_2CH_2OH$, J=5.2 Hz), 3.57–3.92 (t, 4H, 2×$NHCH_2CH_2OH$, J=5.0 Hz), 3.82 (s, 6H, 2×$OCH_3$), 4.64–4.72 (m, 6H, 2×$PhCH_2$ and 2×OH), 6.10–6.16 (t, 2H, 2×NH, J=5.4 Hz), 6.98(s, 4H, 4×Ar-H), 7.13 (s, 2H, 2×Ar-H), 7.59 (t, 2H, 2×NH).

EXAMPLE 33

2,6-Di-(3-hydroxypropoxy)-4,8-di-(N-[4-methoxybenzyl]-N-methyl)aminopyrimidopyrimidine (NU3100)

(a) 1st Stage—Preparation of 3-Triisopropylsilyloxypropan-1-ol

To a stirred solution of imidazole (0.46 g, 6.92 mmol) and propane-1,3-diol (5 ml, 69.16 mmol) in dry DMF (5 ml) was added triisopropylchlorosilane (1.46 ml, 6.92 mmol) dropwise. The reaction mixture was stirred at room temperature under $N_2$ for 36 h, and water (50 ml) was added. The mixture was extracted with ether (3×50 ml), and the organic layers were combined, washed with water (5×50 ml) and dried ($Na_2SO_4$). Evaporation of the solvents in vacuo gave the named product (1.38 g, 92%) as a colourless oil. NMR data was as follows:

$\delta_H$ (200 MHz, $CDCl_3$) 1.02–1.09 (m, 21H, 3×$^i$Pr-H), 1.75–1.83 (q, 2H, $HOCH_2CH_2CH_2$), 2.15 (s, 1H, OH), 3.74–3.84 (m, 2H, $HOCH_2CH_2CH_2$), 3.88–3.94 (t,2H, $HOCH_2CH_2CH_2$).

(b) 2nd Stage—Preparation of 2,6-Di-(3-Triisopropylsilyloxypropoxy)-4,8-di-(N-[4-methoxybenzyl]-N-methyl)aminopyrimidopyrimidine Sodium hydride (0.15 g, 3.90 mmol) was added to a solution of 3-triisopropylsilyloxypropan-1-ol (0.84 g, 3.90 mmol) in dry THF (5 ml) under a $N_2$ atmosphere. The grey suspension was stirred at RT for 10 min, heated to 75° C. for 30 min, and then allowed to cool to ambient temperature. A solution of 2,6-Dichloro-4,8-di-(N-[4-methoxybenzyl]-N-methyl)aminopyrimidopyrimidine (0.39 g, 0.78 mmol) in dry THF (20 ml) was added, and the mixture was heated under reflux for 12 h. After cooling, water was added and the mixture was stirred for 20 min and extracted with ethyl acetate (5×30 ml). The organic layers were combined, dried ($NaSO_4$), and the solvents were evaporated under reduced pressure to afford a yellow oil (0.47 g, 5.3 mmol). This compound was used in the next stage without further purification.

(c) 3rd Stage - Preparation of 2,6-Di-(3-hydroxypropoxy)-4,8-di-(N-[4-methoxybenzyl]-N-methyl)aminopyrimidopyrimidine (NU3100)

Tetrabutylammonium fluoride (1M solution in THF, 2.12 ml, 2.12 mmol, 4 mol. eq.)was added dropwise to a solution of 2,6-di-(3-triisopropylsilyloxypropoxy)-4,8-di- (N-(4-methoxybenzyl] -N-methyl) aminopyrimidopyrimidine (0.47 g, 0.53 mmol) in dry THF (10 ml) and the mixture was stirred at room temperature under a $N_2$ atmosphere for 1 h. Evaporation of solvents furnished a dark yellow oil which was dissolved in water (50 ml), and the aqueous solution was extracted with dichloromethane (4×20 ml). The combined organic layer was dried ($Na_2SO_4$) and solvents were removed in vacuo to give a brown oil. The title compound was isolated by chromatography on silica, employing dichloromethane: methanol (9:1) as eluent, as a pale yellow solid (0.18 g, 6%). The measured NMR data was as follows:

$\delta_H$ (200Mhz, $d_6$-DMSO) 1.77–1.84(t, 4H, 2×$OCH_2CH_2CH_2$, J=6 Hz), 3.34 (s, 6H, 2×$NCH_3$), 3.81 (s, 6H, 2×$OCH_3$), 3.49–3.51 (t, 4H, 2×$OCH_2CH_2CH_2OH$), 4.13 (t, 4H, 2×$OCH_2CH_2CH_2OH$), 4.55–4.60 (t, 2H, 2×OH, J=5 Hz), 5.50 (br S, 4H, 2×$MeOPhCH_2$), 6.96–7.00 (d,<4H, ArH-3, H-5, J=9 Hz), 7.27–7.31 (d, 4H, ArH-2, H-6, J=9 Hz),; m/z (EI) 578 ($M^+$, 44%), 457 ($M^+$—$MeOC_7H_7$), 150 ($MeOC_7H_7NMe^+$), 121 ($MeOCH_7^+$).

Similarly prepared from 2,6-dichloro-4,8-(N-methylbenzylamino)pyrimidopyrimidine and 2-triisopropylsilyloxyethanol was the following:

EXAMPLE 34

2,6-Di-(2-hydroxyethoxy)-4,8-di-(N-benzyl-N-methyl) aminopyrimidopyrimidine (NU3103)

The measured NMR data was as follows:

$\delta_H$ (200 MHz, CDCl$_3$) 1.64 (br s, 1H, OH), 1.98 (br s, 4H, 4×OH), 3.23 (s, 6H, 2×NCH$_3$), 3.62–3.64 (t, 4H, 2×HOCH$_2$CH$_2$O, J=4.5 Hz), 3.89–3.94 (t, 4H,, 2×HOCH$_2$CH$_2$O, J=4.4 Hz), 5.41 (s, 4H, 2×PhCH$_2$), 7.16–7.30 (m, 10H, 10×Ar-H); m/z (EI): 490 (M$^+$, 64%), 475 (M$^+$—CH$_3$), 399 (M$^+$—C$_7$H$_7$), 91 (C$_7$H$_7^+$, 100%), 69 (C$_5$H$_9^+$)

Biological Activity

In vitro activity. Tables 1 and 2 at the end of the present description show in vitro test results obtained in various sets of experiments in which the inhibition of thymidine uptake into L1210 cells (murine leukaemia cell line) grown in culture, both in the absence of and in the presence of AGP was measured for a range of selected compounds of the present invention.

Nucleoside Transport Inhibition Assays

For testing the compounds an established nucleoside transport assay involving measurement of thymidine uptake was adapted. Murine leukaemia L1210 cells were used in this assay as their nucleoside transport characteristics are well known.

This assay for measuring thymidine uptake used a modification of the rapid mixing technique of Wohleheuter, R. M. et al (1978) *Methods in Cell Biology* 20 211–236. The uptake of 100 $\mu$M thymidine by 106 cells was followed at 2 second intervals over a 12 second time course in the presence or absence of inhibitor in 1% or 5% DMSO. In some experiments uptake was also measured in the presence of 5 mg/ml human $\alpha_1$ acid glycoprotein (AGP). This represents the upper limit of concentration of patient plasma AGP and is approximately 125M (M.W. approximately 40,000 Da) i.e. >10× molar excess of inhibitor tested at 10 $\mu$M.

Materials used included a transport buffer comprising 130 mM NaCl, 5 mM KC$_1$, 1 mM MgCl, 5 mM NaH$_2$PO$_4$, 10 mM glucose and 10 mM HEPES. This buffer was made up as sterile 5× concentrate and reconstituted in distilled water and adjusted to pH 7.4 immediately prior to carrying out the assay.

The L1210 cells were generally prepared as follows:

300 ml of L1210 cells in exponential growth phase (<8×10$^5$ cells/ml) grown in RPMI 1640 medium supplemented with 10% foetal calf serum were centrifuged at 1000 rpm for 5 minutes at 4° C. The supernatant was aspirated and the cells were washed with ice-cold transport buffer and centrifuged again at 1000 rpm for 5 minutes at 4° C. The supernatant was removed and the cells were resuspended in ice-cold transport buffer to give a final cell density of 2–4×10$^7$ cells/mi. Cells were left on ice for 30 minutes recovery prior to starting the assay.

In a typical procedure for carrying out the thymidine uptake transport assay, 333 $\mu$l of cell suspension and 323 $\mu$l transport buffer (±15.46 mg/ml AGP) were incubated with 10 $\mu$l inhibitor (dissolved in DMSO at 100× the desired final concentration) or 10 $\mu$l DMSO (control) for at least 5 minutes at 21° C. For less soluble compounds the DMSO concentration was increased, in which case 333 $\mu$l cells and 2831 $\mu$l (±17.65 mg/ml AGP) transport buffer were incubated with 50 $\mu$l of inhibitor (at 20× the desired final concentration) or 50 $\mu$l DMSO. The suspension was mixed well and 100 $\mu$l was layered onto 150 $\mu$l silicone oil (9:11 Dow Corning 556 (Sp.Gr. 0.98):Dow Corning 550 (Sp.Gr. 1.068) (final Sp.Gr. 1.028) overlaying 50 $\mu$l 3M KOH in 6 replicate 0.5 ml microfuge tubes. Transport was initiated by adding 50 $\mu$l of 300 $\mu$M thymidine in transport buffer labelled with 25 $\mu$Ci/ml [methyl-$^3$H]thymidine and 2 $\mu$Ci/ml [$^{14}$C] sucrose to each tube in turn at one second intervals in time to a metronome set at 60 beats/minute using an Eppendorf multipette with a 1.25 ml tip. Following a wait beat, transport was stopped by the addition of 50$\mu$ of 400 $\mu$M dipyridamole in transport buffer (acidified with HCl) at one second intervals to the tubes in reverse order. The tubes were immediately transferred to a microfuge (Eppendorf) and spun at 12000 rpm for 2 minutes to pellet the cells through the oil and into the KOH. The tubes were capped and the cells left to solubilise in the KOH for 1 hour. Cell number and viability for each run was determined by haemocytometer counting using trypan blue exclusion. At least two positive control incubations 1 $\mu$M or 10 $\mu$M dipyridamole were included in each experiment. The tubes were capped and cut in the oil layer such that the bottom portion (cells solubilised in KOH) fell into a 20 ml scintillation vial. 1 ml 0.25M acetic acid followed by 1 ml air was injected into the tube using a 2 ml syringe and 23-gauge needle to disperse and neutralise the KOH-solubilised cells. 10 ml of Optiphase HiSafe™ scintillant was added and the vials capped and shaken. Triplicate 10 $\mu$l aliquots of the 300 $\mu$M thymidine±25 $\mu$Ci/ml [methyl-$^3$H]thymidine and 2 $\mu$Ci/ml [$^{14}$C] sucrose were also counted as standards. The [$^{14}$C]:[$^3$H] ratio was used to calculate the amount of non-transported contaminating [$^3$H]thymidine in the extracellular space. The accumulation of [$^3$H]thymidine was calculated as pmol/10$^6$ viable cells.

The rate of thymidine uptake in the presence and absence of inhibitor was calculated from linear regression of pmol thymidine/10$^6$ cells vs time (in seconds) using GraphPad PRIZM™ software and comparison of rates in the presence of inhibitor with rate in the absence of inhibitor gave the % inhibition of uptake.

The results of these assays are given in Table 1 which is a full tabulated list of compounds that have been made including NU reference numbers, structures and membrane transport inhibition data with results in some cases obtained in different experiments for different concentrations of the compounds. Further data for selected compounds tested for inhibition of nucleoside transport at 1 and 10 $\mu$M concentration in the presence of 5 mg/ml AGP are given in Table 2.

It will be seen that 10 $\mu$M dipyridamole inhibited thymidine uptake by approximately 100% in the absence of AGP but this was virtually abolished in the presence of AGP. The effect of AGP on the inhibition of thymidine uptake by other analogues was significantly less than for dipyridamole and in the case of NU3076, NU3077, NU3084 and NU3087, for example, there was no significant reduction of inhibition by AGP. Moreover, NU3076 and NU3084 at least appear to be more potent inhibitors than dipyridamole both in the presence and absence of AGP or, as found in other assays, in the presence or absence of 40 mg/ml human serum albumin.

Growth Inhibition Assays

In addition to identifying compounds that inhibit nucleoside transport some have also been tested for their ability to inhibit thymidine rescue of thymidylate synthase-inhibited cells, using L1210 cells again and the antifolate drug known as CB3717.

The antifolate, CB3717, inhibits cell growth by inhibiting thymidylate synthase (TS) which is responsible for the conversion of dUMP to dTMP that is later phosphorylated to dTTP for DNA synthesis. Inhibition of TS results in the depletion of intracellular dTTP and, because of an increase of dUMP behind the block, an increase in dUTP which causes DNA strand breakage (see Curtin et al, *Cancer Research*, 51 2346–2353, 1991). Salvage of extracellular thymidine through nucleoside transport and thymidine kinase activity can provide the necessary dTMP and hence rescue the cell. Inhibition of nucleoside transport potentiates the activity of TS inhibitors by preventing the efflux of deoxyuridine, leading to a greater accumulation of dUTP and by preventing rescue by the uptake of exogenous thymidine.

In carrying out these growth inhibition assays, L1210 cells were adapted to growth in RPMI 1640 medium supplemented with 10% dialysed serum (dialysed for 24 hours at 4° C. against 2 changes of 9 volumes of PBS containing 1 g activated charcoal/L and a further 2 changes of 9 volumes of PBS). All experiments were performed using medium supplemented with dialysed serum to remove exogenous nucleosides.

Cells in log phase growth were suspended at $4 \times 10^4$ cells/ml, and solutions of CB3717, thymidine and inhibitor were prepared at 4× the final desired concentration in RPMI 1640+10% dialysed serum. Concentrated stocks of the inhibitors were dissolved in DMSO, the DMSO concentration was controlled so as to be present at 0.1% in the final incubation except where indicated. 0.25 ml cell suspension, 0.25 ml medium±CB3717, 0.25 ml medium±thymidine and 0.25 ml medium±inhibitor were dispensed into each well of a 24 well plate (4–6 replicate wells/drug contamination). Replicate 0.25 ml aliquots of the remaining cell suspension were counted to obtain a time 0 cell count. After incubation at 37° C. for 48 hours (to allow for a minimum of 3 cell doublings) cells were enumerated using a Coulter counter Model Z1.

The results of these assays in which the growth inhibition of L1210 cells by CB3717 was measured in the presence and absence of inhibitor (concentration 0, 1 and 10 $\mu$M), and with and without 1 $\mu$M thymidine, showed that all the inhibitors increased the growth inhibition by CB3717 and could block to a varying extent the thymidine rescue. Thus, it was demonstrated that enhancement of thymidylate synthase inhibitor cytotoxicity and prevention of thymidine rescue, as evidenced by potentiation of CB3717 growth inhibition, is related to the extent and potency of nucleoside transport inhibition produced by the dipyridamole analogue concerned.

In general, the studies carried out fully support the belief that the nucleoside transport inhibitory characteristics of the compounds tested reflect an ability of these compounds to potentiate the cytotoxicity of antimetabolite agents, such as certain cytotoxic antitumour drugs used in cancer therapy.

Accordingly, having regard to their significant nucleoside transport inhibitory characteristics and reduced binding affinity for AGP (as compared to dipyridamole), the compounds of this invention can be expected to be especially useful in vivo for administration in conjunction with such cytotoxic drugs in order to potentiate the cytotoxic effect of the latter in the course of medical treatment, as hereinbefore indicated.

As mentioned earlier in this specification further information and data obtained from recent work investigating inhibition of purine uptake, particularly hypoxanthine, by dipyridamole and the effect of this in relation to selective potentiation of cytotoxic antifolate agents has now been published in the documents referred to. Although the newly published data relates particularly to dipyridamole, tests carried out on dipyridamole analogues disclosed herein, especially compound NU3076, have shown a behaviour similar to dipyridamole, at least in respect of preventing hypoxanthine rescue from LY309887 (an analogue of the antifolate drug lometerxol) growth inhibition for selected tumour cell lines. For example, in investigating the compound NU3076, two lung cancer cell lines: A549 and COR L23 and two breast cancer cell lines MCF7 and MDA MB231 were selected for study. All cell lines were adapted to growth in dialysed serum as previously referred to. In earlier experiments, it had been shown that dipyridamole blocked hypoxantine rescue from lometerxol growth inhibition in A549 and MCF7 but not in COR L23 and MDA MB231. In these further investigations, all cell lines were seeded into 96-well plates and drug incubation periods were between 72 and 144 hours depending on the growth rate of the cell under study, sufficient to ensure that control cultures had undergone at least 3 cell doublings. Cells were exposed to varying concentrations of LY309887 in the presence or absence of 10 $\mu$M hypoxanthine, with or without 3 $\mu$M NU3076. At the end of the exposure period the cells were fixed and stained with sulphorhodamine B. Hypoxanthine protected all the cell lines from LY309887 growth inhibition. NU3076 prevented hypoxanthine rescue in A549 and MCF7 cells but not COR L23 and MDA MB231. Thus, the cells displayed the same differential sensitivity to NU3076 as they do to dipyridamole, but most importantly the results have again demonstrated the therapeutic potential of certain dipyridamole analogues, again emphasising the desirability of enlarging the available range of such compounds.

As will be seen, overall the invention provides a number of different aspects and it embraces each and every novel and inventive feature and aspect herein disclosed, either explicitly or implicitly and either singly or in combination with one another. Moreover, the scope of the invention is not to be construed as being limited by the illustrative examples or by the terms and expressions used herein merely in a descriptive or explanatory sense.

TABLE 1

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3003 | 2,6-bis-(diethanolamino)-4,8-dipiperidino-pyrimidopyrimidine C$_{24}$H$_{40}$N$_8$O$_4$ MW = 504.64 | 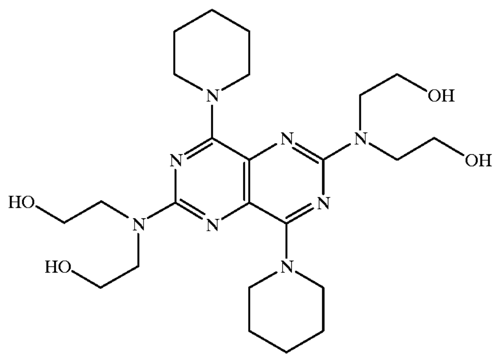 | 1 10 | 80 ± 8 (26) 99 ± 2 (84) IC$_{50}$ = .36 μM IC$_{50}$ = .37 μM | +40 mg/ml HSA 100, 100 | 13 ± 12 (27) |
| NU3064 | 2,6-di-n-propoxy-4,8-dipiperidino-pyrimidopyrimidine C$_{22}$H$_{34}$N$_6$O$_2$ MW = 414.5 | 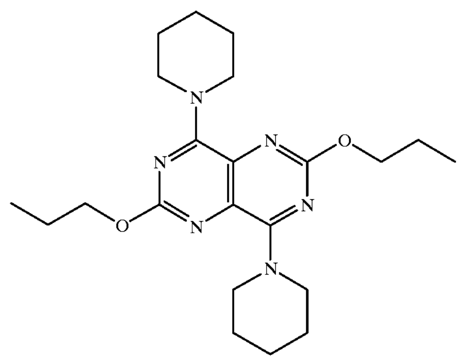 | 10 100 | 37 ± 11 (5) 60 ± 9 (6) IC$_{50}$ = 52 μM | | |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3065 | 2,6-bis[2,2-diethoxy]-n-propoxy-4,8-dipiperidino-pyrimidopyrimidine<br>$C_{30}H_{50}N_6O_6$<br>MW = 590 | 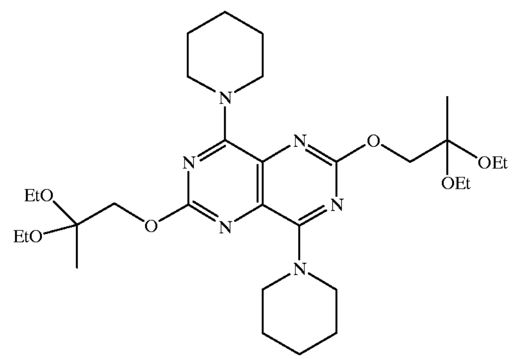 | 1<br>10<br>100 | 30 ± 7 (3)<br>65 ± 9 (3)<br>82 ± 16 (3)<br>$IC_{50}$ = 4.24 μM | | |
| NU3066 | 2,6-di[2-oxo]-n-propoxy-4,8-dipiperidino-pyrimidopyrimidine<br>$C_{22}H_{30}N_6O_4$<br>MW = 442.5 | 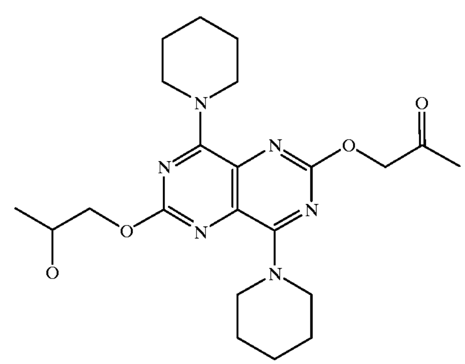 | 10 | 58 ± 3 (3)<br>(5% DMSO) | | |

TABLE 1-continued

| House No. | Name | Structure | Conc (µM) | % Inhibition of ³H-thymidine uptake | | |
|---|---|---|---|---|---|---|
| | | | | No AGP | +1 mg/ml AGP | +5 mg/ml AGP |
| NU3067 | 2,6-dimethoxy-4,8-dipiperidino-pyrimidopyrimidine C₁₈H₂₆N₆O₂ MW = 358 | 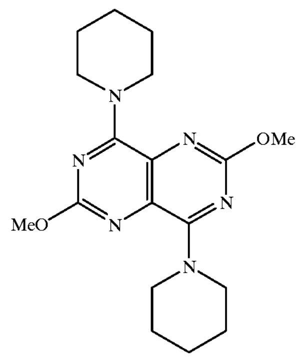 | 10 50 | 39 ± 7 (3) 81, 76 (5% DMSO) | | |
| NU3068 | 2,6-diethoxy-4,8-dipiperidino-pyrimidopyrimidine C₂₀H₃₀N₆O₂ MW = 386 | 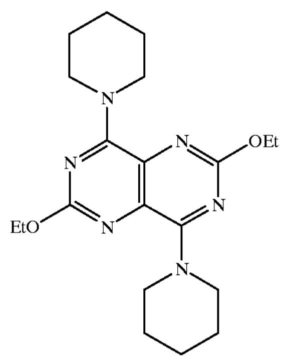 | 10 50 | 35 ± 4 (3) 74, 65 (5% DMSO) | | |

TABLE 1-continued

| House No. | Name | Structure | % Inhibition of ³H-thymidine uptake | | | |
|---|---|---|---|---|---|---|
| | | | Conc (μM) | No AGP | +1 mg/ml AGP | +5 mg/ml AGP |
| NU3069 | 2,6-di-iso-propoxy-4,8-dipiperidino-pyrimidopyrimidine C₂₂H₃₄N₆O₂ MW = 414.5 | 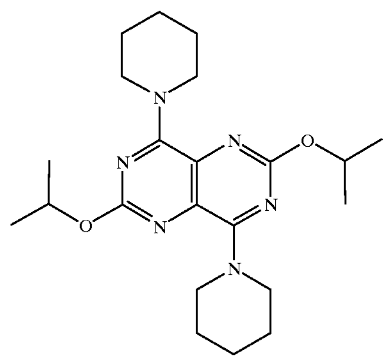 | 10 100 | 23 ± 12 (3) 64 ± 6 (3) (5% DMSO) | | |
| NU3070 | 2,6-di-3-methylbutoxy-4,8-dipiperidino-pyrimidopyrimidine C₂₆H₄₂N₆O₂ MW = 470.65 | 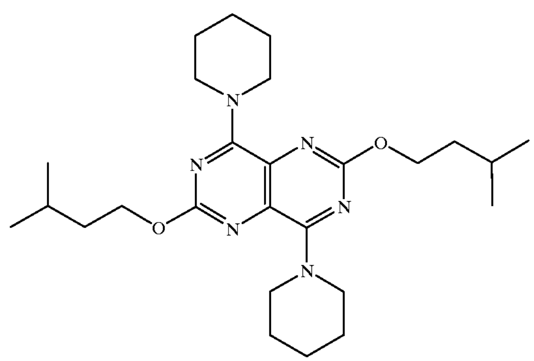 | 10 | 46, 51 (5% DMSO) | | |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3071 | 2,6-di-iso-butoxy-4,8-dipiperidino-pyrimidopyrimidine C₂₄H₃₈N₆O₂ MW = 442.6 | 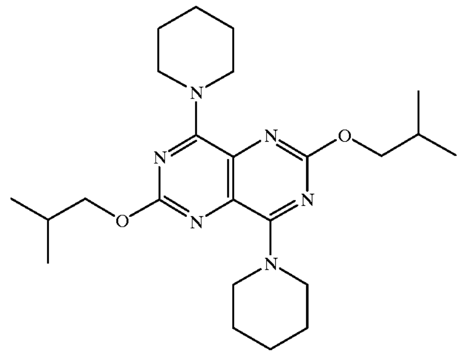 | 10 100 | 25 ± 4 (3) 65 ± 4 (3) (5% DMSO) | | |
| NU3072 | 2,6-diallyl-4,8-dipiperidino-pyrimidopyrimidine C₂₂H₃₀N₆O₂ MW = 410.51 | 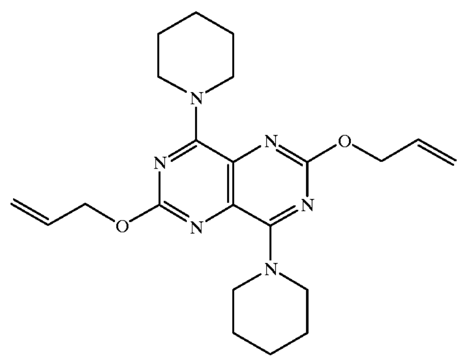 | 10 100 | 52 ± 7 (3) 66, 63 (5% DMSO) | | |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3074 | 2,6-di-(2-methoxy-1-methyl)ethoxy-4,8-dipiperidino-pyrimidopyrimidine<br>$C_{24}H_{38}N_6O_4$<br>MW = 474.60 | 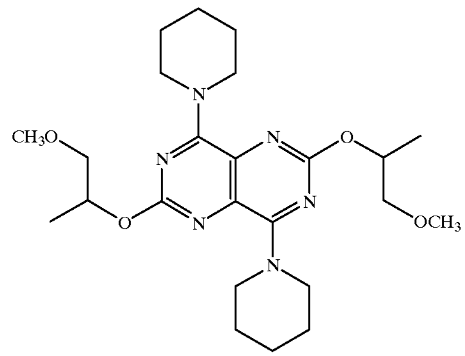 | 10<br>100 | 62 ± 10 (3)<br>96 ± 7 (3) | | |
| NU3075 | 2,6-dichloro-4,8-di-N-tetrahydroisoquinolinyl-pyrimidopyrimidine<br>$C_{24}H_{20}N_6O_2$<br>MW = 463.36 | 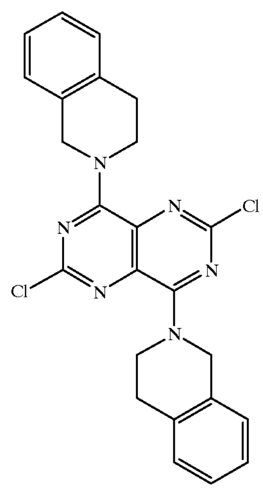 | | NT | | |

TABLE 1-continued

| House No. | Name | Structure | Conc (μM) | % Inhibition of ³H-thymidine uptake | | | |
|---|---|---|---|---|---|---|---|
| | | | | No AGP | +1 mg/ml AGP | +40 mg/ml HSA | +5 mg/ml AGP |
| NU3076 | 2,6-bis-diethanolamino-4,8-di-(4-methoxybenzyl-amino)pyrimidopyrimidine $C_{30}H_{40}N_8O_6$ MW = 608.69 | 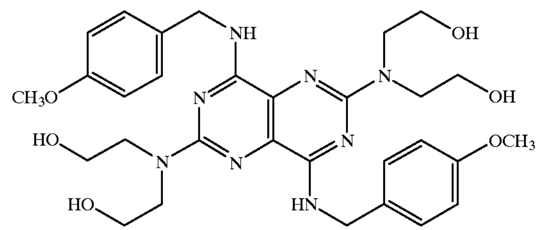 | 1 10 | 65 ± 11 (16) 96 ± 8 (18) $IC_{50}$ = .253 ± .075 μM (3) | | +40 mg/ml HSA 89 ± 10 (3) | 46 ± 8 (7) 89 ± 14 (9) |
| NU3077 | 2,6-di-(2-hydroxypropoxy)-4,8-dipiperidino-pyrimidopyrimidine $C_{22}H_{34}N_6O_4$ MW = 446.54 | 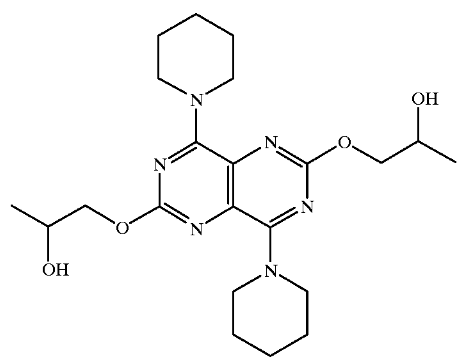 | 1 10 | 47 ± 8 (9) 92 ± 10 (6) $IC_{50}$ = .9 μM $IC_{50}$ = 1.13 μM | | | 20 ± 10 (3) 69 ± 9 (3) |
| NU3078 | 2,6-disolketalo-4,8-dibenzylaminopyrimido-pyrimidine $C_{32}H_{38}N_6O_6$ MW = 602.69 | 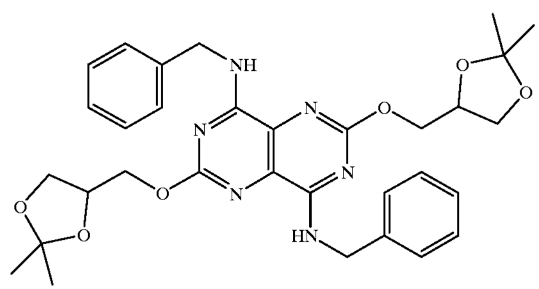 | 10 | 46 ± 3 (3) | | | |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3079 | 2,6-bis-diethanolamino-4,8-di-(4-trifluoromethyl-benzylamino)pyrimidopyrimidine $C_{30}H_{34}N_8O_4F_6$ MW = 684.64 | 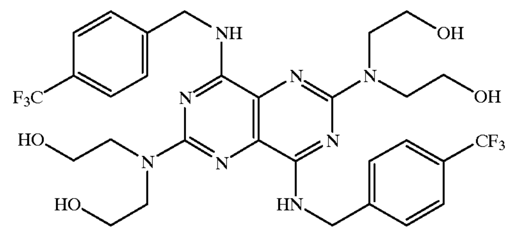 | 1 10 | 32 ± 11 (3) 60 ± 7 (3) | | |
| NU3080 | 2,6-diethanolamino-4,8-di-N-tetrahydroisoquinolyl-pyrimidopyrimidine $C_{32}H_{40}N_8O_4$ MW = 600.72 | 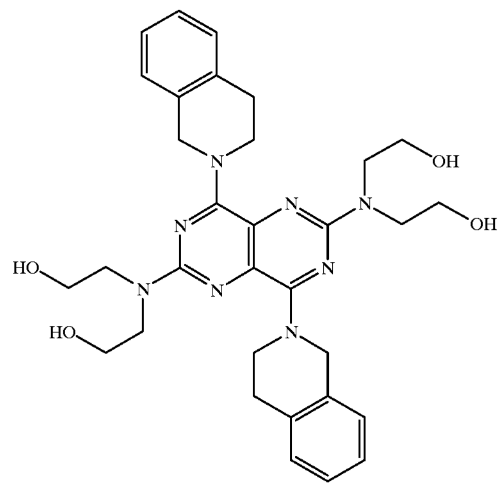 | 1 10 | 72 ± 22 (15) 100 ± 0 (9) $IC_{50}$ = 0.72 ± 0.38 μM | | 69 ± 7.5 (6) |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3081 | 2-chloro-6-diethanolamino-4,8-bis[(3,4-dimethoxybenzyl)amino]pyrimidopyrimidine $C_{28}H_{34}N_7O_6Cl$ MW = 600.07 | 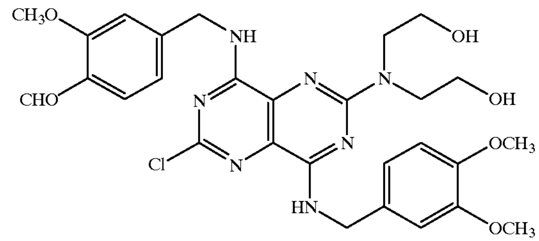 | 1 10 | 59 ± 2 (6) 95 ± 9 (3) $IC_{50}$ = 0.71 μM | | |
| NU3082 | 2-chloro-6-diethanolamino-4,8-di-N-tetrahydroisoquinolyl pyrimidopyrimidine $C_{28}H_{30}N_7O_2Cl$ MW = 532.04 | 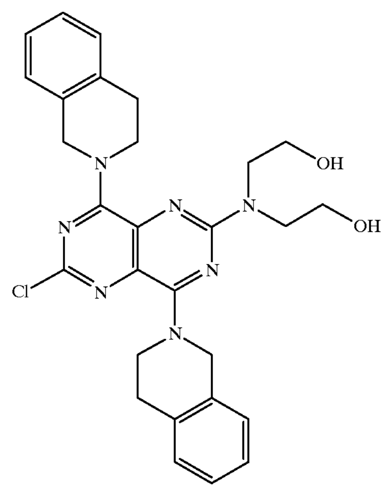 | 1 10 | 9, 0, 0 22 ± 14 (3) | | |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3083 | 2,6-bis(diethanolamino)-4,8-di(4-chlorobenzyl-amino)pyrimidopyrimidine C₂₈H₃₄N₈O₄Cl₂ MW = 617.53 | 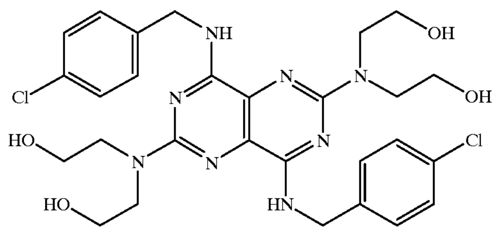 | 1 10 | 53 ± 15 (9) 92 ± 14 (3) IC₅₀ = 1.11 μM | | |
| NU3084 | 2,6-bis-diethanolamino-4,8-bis-(3,4-dimethoxy-benzylamino)pyrimido-pyrimidine C₃₂H₄₄N₈O₈ MW = 668.75 | 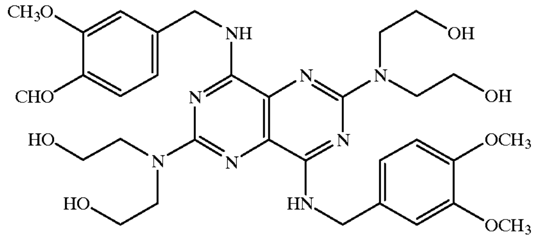 | 1 10 | 74 ± 16 (9) 98 ± 5 (12) IC₅₀ = 0.25 μM | | 64 ± 3 (3) 93 ± 10 (9) |
| NU3085 | 2,6-di-(3-hydroxy-propoxy)-4,8-dipiperidino-pyrimidopyrimidine C₂₂H₃₄N₆O₄ MW = 446.54 | 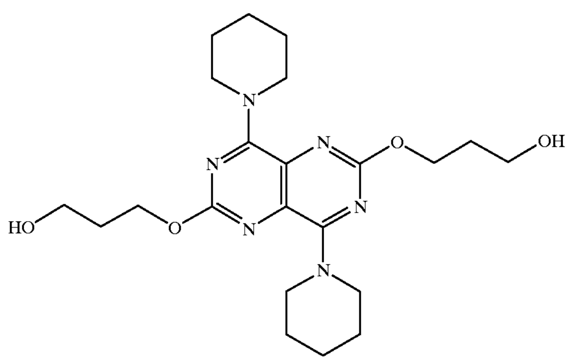 | 1 10 | 35 ± 5 (5) 100, 76 IC₅₀ = 2.36 μM | | |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3086 | 2,6-di-(2-hydroxyethoxy)-4,8-dipiperidino pyrimidopyrimidine $C_{20}H_{30}N_6O_4$ MW = 418.49 | 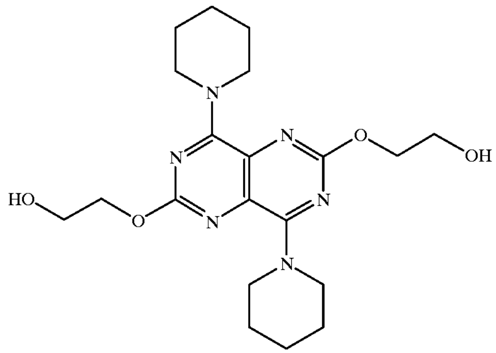 | 1 10 100 | 13.3 ± 6 (3) 61 ± 6 (3) 100 ± (3) $IC_{50}$ = 6.3 μM | | |
| NU3087 | 2,6-di-(2-hydroxypropoxy)-4,8-di-(4-methoxybenzyl-amino)pyrimidopyrimidine $C_{28}H_{34}N_6O_6$ MW = 550.61 | 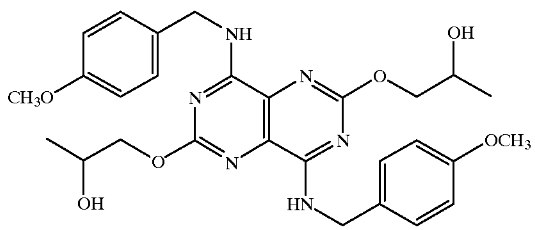 | 1 0.25 | 68 ± 14 (9) $IC_{50}$ = 0.3 μM estimate - solubility problems 17 ± 6 (3) | | +0.125 mg/ml AGP 20 ± 2 |
| NU3088 | 2,6-di-(3-hydroxy-propoxy)-4,8-di-(N-benzylmethylamino)-pyrimidopyrimidine $C_{28}H_{34}N_6O_4$ MW = 518.61 | 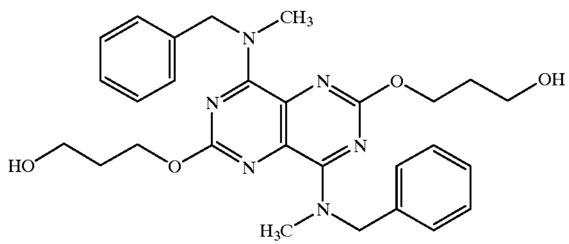 | 1 10 | 52 ± 19 (8) 100, 77, 100 $IC_{50}$ = 1.44 μM | | |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3089 | 2,6-di-(2-hydroxyethoxy)-4,8-di-(N-4-methoxy-benzylamino)-pyrimidopyrimidine C₂₈H₃₄N₉O₄Cl₂ MW = 617.53 | 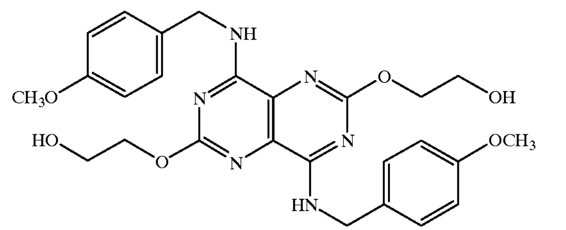 | 1 10 | 40 ± 19 (11) 88 ± 11 (3) IC₅₀ = 0.67 μM IC₅₀ = 1.2 μM | | 28 ± 25 (5) |
| NU3090 | 2,6-di-(3-hydroxy-propoxy)-4,8-di-(N 4-methoxybenzyl-N-methyl-amino)pyrimidopyrimidine C₃₀H₃₈N₆O₆ MW = 578.66 | 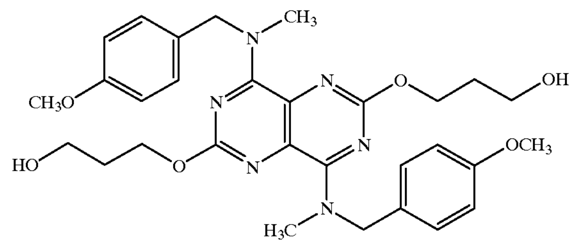 | 1 10 | 74 ± 18 (11) (88) 100 ± 0 (3) figs in parenthesis are for NU3100, which was a repeat synthesis IC₅₀ = 0.22 μM 0.24 μM (0.19 μM) | | 32 ± 10 (8) |
| NU3091 | 2,6-dipropoxy-4,8-di-(N-benzyl-N-methylamino)-pyrimidopyrimidine C₂₈H₃₄N₆O₂ MW = 481.61 | 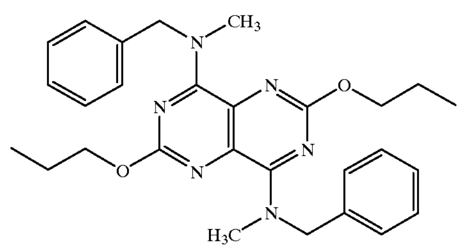 | 1 10 | Inactive 8.2 ± 1.1 (3) | | |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3092 | 2,6-di-(2-methoxyethoxy)-4,8-di-(N-benzyl-N-methylamino)pyrimidopyrimidine C₂₈H₃₄N₆O₄ MW = 518.61 | 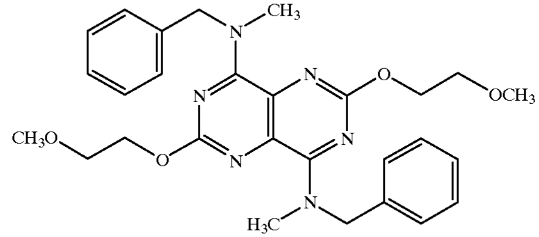 | 1 10 | 17 ± 8 (9) 68 ± 8 (9) IC₅₀ = 5.9 μM 3.8 μM | | |
| NU3093 | 2,6-di-(2-methoxyethoxy)-4,8-dipiperidino-pyrimidopyrimidine C₂₂H₃₄N₆O₄ MW = 446.54 | 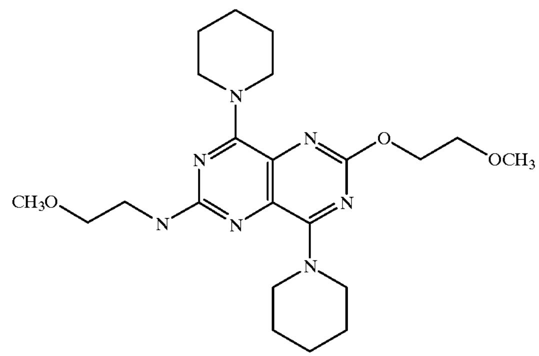 | 1 10 | 20 ± 6 (3) 63, 68 IC₅₀ = 4.6 μM | | |

TABLE 1-continued

| House No. | Name | Structure | Conc (µM) | % Inhibition of ³H-thymidine uptake | | |
|---|---|---|---|---|---|---|
| | | | | No AGP | +1 mg/ml AGP | +5 mg/ml AGP |
| NU3094 | 2,6-di((-2-methoxyethoxy)-4,8-bis(dibenzylamino)pyrimidopyrimidine $C_{40}H_{42}N_6O_4$ MW = 670.81 | 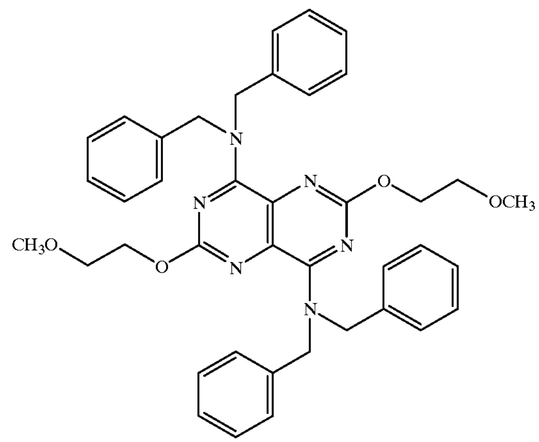 | 1 10 | 9 ± 10 (3) 15 ± 4 (3) | | |
| NU3095 | 2,6-di((-2-methoxyethoxy)-4,8-dibenzylamino pyrimidopyrimidine $C_{26}H_{30}N_6O_4$ MW = 490.56 | 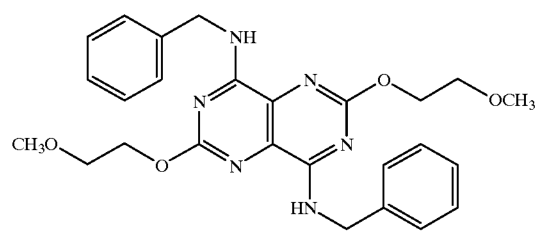 | 1 10 | 31.2 ± 19.1 (3) 78.4 ± 4.2 (3) $IC_{50}$ = 2.4 µM | | |
| NU3096 | 2,6-di((-3-hydroxypropoxy)-4,8-bis[(-3,4-dimethoxybenzyl)-N-methylamino]pyrimidopyrimidine $C_{32}H_{42}N_6O_8$ MW = 638.72 | 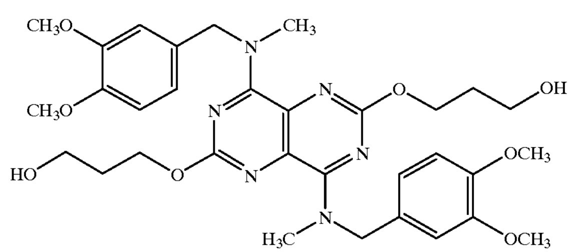 | 1 | 54 ± 2 (3) $IC_{50}$ = 0.75 µM | | |

TABLE 1-continued

| House No. | Name | Structure | Conc ($\mu$M) | % Inhibition of $^3$H-thymidine uptake | | |
|---|---|---|---|---|---|---|
| | | | | No AGP | +1 mg/ml AGP | +5 mg/ml AGP |
| NU3097 | 2,6-di(-3-hydroxy-propoxy)-4,8-di(-4-methoxybenzylamino)pyrimidopyrimidine $C_{28}H_{34}N_8O_6$ MW = 550.61 | 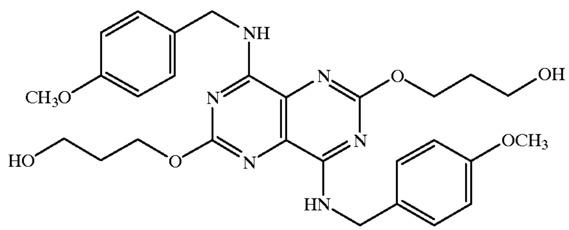 | 1 | 61 ± 8 (11) $IC_{50}$ = 0.46 $\mu$M $IC_{50}$ = 0.82 $\mu$M | | 49 ± 7 (8) |
| NU3098 | 2,6-di(-2-hydroxyethoxy)-4,8-di(N-methylbenzylamino)pyrimidopyrimidine $C_{26}H_{30}N_6O_4$ MW = 490.56 | 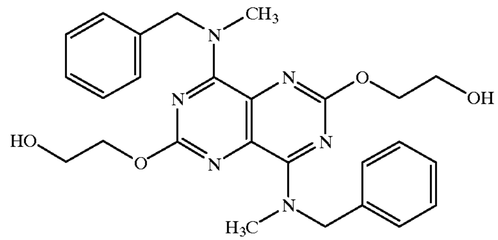 | 0.1 1 10 | (12, 18) 44 ± 7 (3) (50, 60) 87 ± 11 (3) (90, 84) (figs in parenthesis are for NU3103) $IC_{50}$ = 1.87 $\mu$M ($IC_{50}$ = 1.01 $\mu$M) $IC_{50}$ = 0.8 $\mu$M) | | (21, 23) |
| NU3099 | 2,6-di(-2-hydroxyethyl)-amino-4,8-di(4-methoxy-benzylamino)pyrimido-pyrimidine $C_{26}H_{32}N_8O_4$ MW = 520.59 | 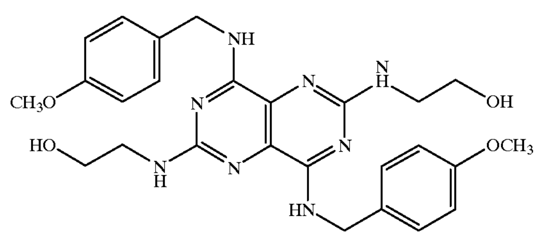 | 0.1 1 | 5 54, 52 62, 65 $IC_{50}$ = 0.93 $\mu$M $IC_{50}$ = 1.2 $\mu$M | | 30, 35 |

TABLE 1-continued

| House No. | Name | Structure | Conc (μM) | % Inhibition of ³H-thymidine uptake | | |
|---|---|---|---|---|---|---|
| | | | | No AGP | +1 mg/ml AGP | +5 mg/ml AGP |
| NU3101 | 2,6-di(-2-hydroxyethyl-amino)-4,8-dibenzyl-aminopyrimidopyrimidine C₂₅H₃₀N₈O₂ MW = 474.56 | 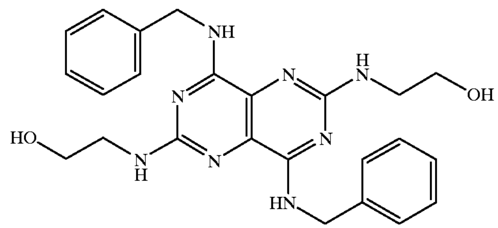 | 0.1 1.0 | 2 58 IC₅₀ = 0.10 μM IC₅₀ = 0.13 μM IC₅₀ = 0.75 μM | | |
| NU3102 | 2,6-bis-diethanolamino-4,8-di-(N-methyl-N-[4-methoxybenzyl]amino-pyrimidopyrimidine C₃₂H₄₄N₈O₆ MW = 636.75 | 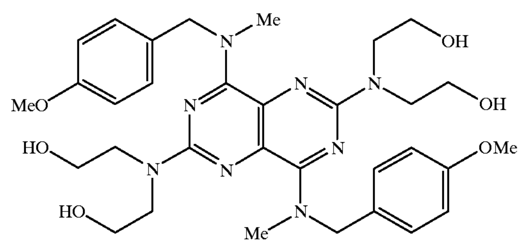 | 0.1 1.0 10 | 23, 20 51, 57 insoluble IC₅₀ = 0.98 μM IC₅₀ = 0.84 μM | | |
| NU3104 | 2,6-di(2-hydroxyethyl)-amino-4,8-bis-(3,4-dimethoxybenzyl)amino-pyrimidopyrimidine C₂₈H₃₆N₈O₆ MW = 580.64 | 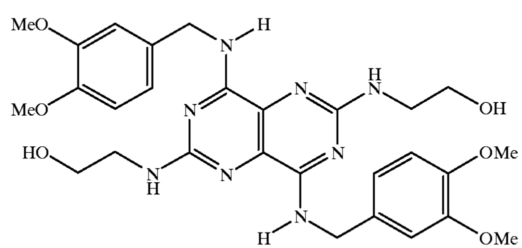 | | | | |

TABLE 2

| House No. | Name | Structure | Conc (μM) | % Inhibition of ³H-thymidine uptake | | % Reduction (*) = p < .05, (NS) = not sig |
|---|---|---|---|---|---|---|
| | | | | No AGP | +5 mg/ml AGP | |
| NU3003 | 2,6-bis-(diethanolamino)-4,8-dipiperidino-pyrimidopyrimidine $C_{24}H_{40}N_8O_4$ MW = 504.64 | 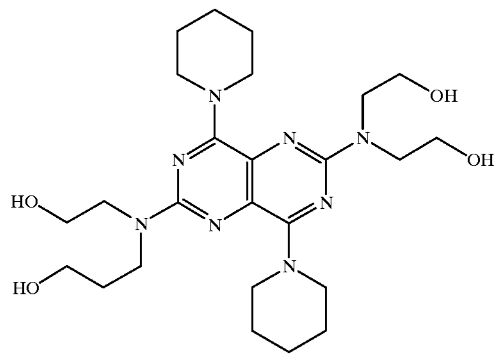 | 10 | 99 ± 2 (84) | 13 ± 12 (27) | 87 (*) |
| NU3076 | 2,6-bis-diethanolamino-4,8-di-(4-methoxybenzylamino)pyrimidopyrimidine $C_{30}H_{40}N_8O_6$ MW = 608.69 | 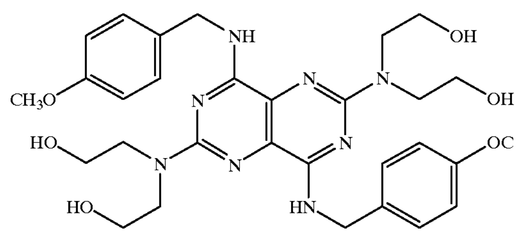 | 10 1 | 96 ± 7 (18) 56 ± 10 (7) | 89 ± 14 (9) 46 ± 8 (7) | 7 (NS) 18 (NS) |

TABLE 2-continued

| House No. | Name | Structure | Conc (µM) | % Inhibition of ³H-thymidine uptake | | % Reduction (*) = p < .05, (NS) = not sig |
|---|---|---|---|---|---|---|
| | | | | No AGP | +5 mg/ml AGP | |
| NU3077 | 2,6-di-(2-hydroxypropoxy)-4,8-dipiperidino-pyrimidopyrimidine $C_{22}H_{34}N_6O_4$ MW = 446.54 | 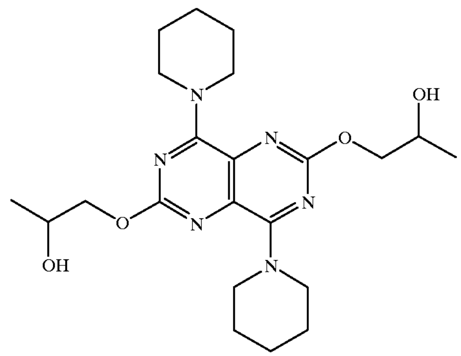 | 10 1 | 92 ± 10 (6) 44 ± 8 (3) | 69 ± 9 (3) 20 ± 10 (3) | 25 (*) 55 (*) |
| NU3080 | 2,6-diethanolamino-4,8-di-N-tetrahydroisoquinolyl-pyrimidopyrimidine $C_{32}H_{40}N_8O_4$ MW = 600.72 | 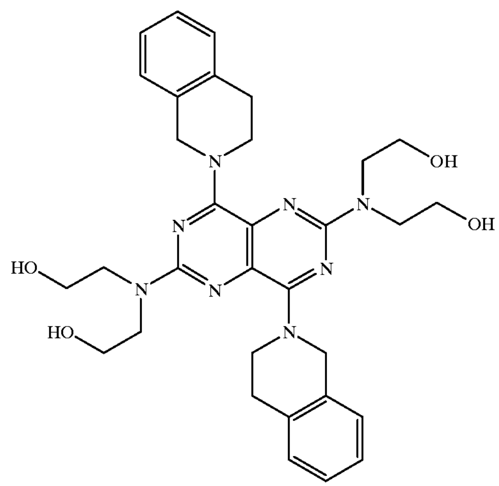 | 10 | 100 ± 0 (3) | 69 ± 7.5 (6) | 31 (*) |

TABLE 2-continued

| House No. | Name | Structure | Conc (μM) | % Inhibition of ³H-thymidine uptake | | % Reduction (*) = p < .05, (NS) = not sig |
|---|---|---|---|---|---|---|
| | | | | No AGP | +5 mg/ml AGP | |
| NU3084 | 2,6-bis(diethanolamino)-4,8-[(3,4-dimethoxybenzyl)amino] pyrimidopyrimidine | 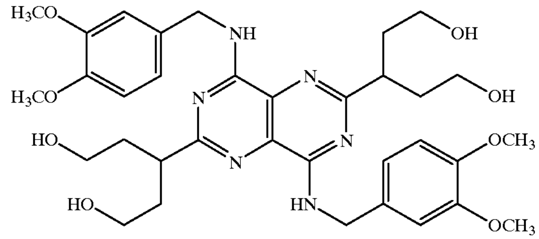 | 10<br>1 | 98 ± 6 (12)<br>67 ± 10 (3) | 93 ± 10 (9)<br>64 ± 3 (3) | 5 (NS)<br>4 (NS) |
| NU3087 | 2,6-di(3-hydroxypropoxy)-4,8-di[(4-methoxybenzyl)amino] pyrimidopyrimidine | 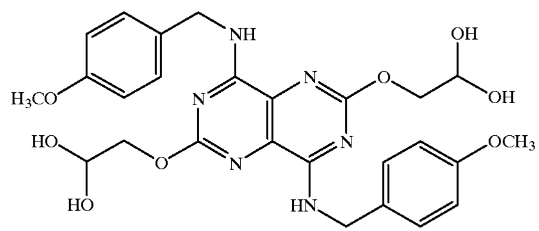 | 0.25 | 17 ± 6 (3) | +0.125 mg/ml AGP<br>20 ± 2 | 0 (NS) |
| NU3089 | 2,6-di(2-hydroxyethoxy)-4,8-di[(4-methoxybenzyl)amino] pyrimidopyrimidine | 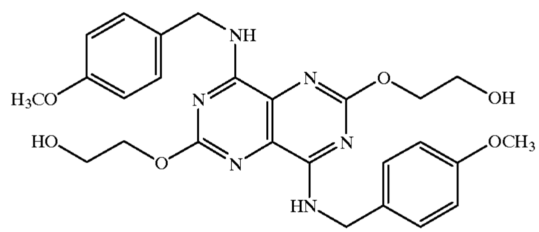 | 1 | 24 ± 18 (5) | 28 ± 25 (5) | 0 (NS) |

TABLE 2-continued

| House No. | Name | Structure | Conc (μM) | % Inhibition of $^3$H-thymidine uptake | | % Reduction (*) = p < .05, (NS) = not sig |
|---|---|---|---|---|---|---|
| | | | | No AGP | +5 mg/ml AGP | |
| NU3090 | 2,6-di(3-hydroxypropoxy)-4,8-di[(4-methoxybenzyl)methylamino]pyrimidopyrimidine | 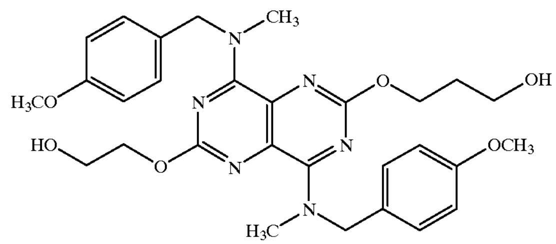 | 1 | 69 ± 19 (8) | 32 ± 10 (8) | 53 (*) |
| NU3097 | 2,6-di(-3-hydroxypropoxy)-4,8-di(-4-methoxybenzylamino)pyrimidopyrimidine $C_{28}H_{34}N_6O_6$ MW = 550.61 | 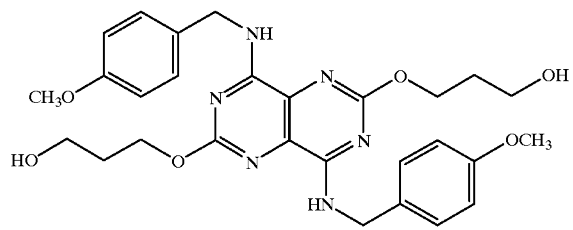 | 1 | 62 ± 6 (8) | 49 ± 7 (8) | 21 (*) |

What is claimed is:

1. A pyrimidopyrimidine compound which is a compound having the structural formula I

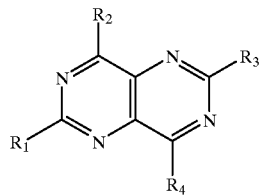

or a pharmaceutically acceptable salt thereof,
characterised in that in structural formula I
$R_1$ and $R_3$ are identical and are selected from allyl, diethanolamino, solketalo and a group having the formula —O—$R_Z$ or —$NHR_z$,
$R_Z$ being selected from alkyl, hydroxyalkyl, alkoxyalkyl, dialkoxyalkyl and 2-oxo-alkyl wherein the or each alkyl and/or alkoxy moiety has less than six carbon atoms, and
$R_2$ and $R_4$ are identical and are selected from N-tetrahydroisoquinolyl, and a benzylamino group having the structural formula II

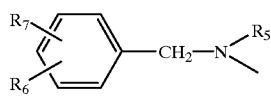

where
$R_5$ is H, or an optionally substituted alkyl or benzyl group, and
$R_6$ and $R_7$ represent H or optional substituents in the aromatic nucleus selected from halo, alkyl, alkoxy, hydroxy, trifluoromethyl, azido, cyano, nitro, carboxyl, carboxylic ester, amino or a substituted amino $NR_xR_y$ where $R_x$ and $R_y$ each represent hydrogen or alkyl, subject to the proviso that
if $R_1$ and $R_3$ are both diethanolamino, $R_2$ and $R_4$ do not correspond to structure II with $R_5$, $R_6$ and $R_7$ each being hydrogen and provided further that, if $R_1$ and $R_3$ are —$NHR_z$ and $R_2$ and $R_4$ are both benzylamino groups of formula II, $R_5$ is hydrogen.

2. A pyrimidopyrimidine compound according to claim 1 wherein each alkyl group present contains 1–5 carbon atoms.

3. A pyrimidopyrimidine as claimed in claim 1 or 2, wherein $R_2$ and $R_4$ are N-tetrahydroisoquinolyl and $R_1$ and $R_3$ are each diethanolamino.

4. A pyrimidopyrimidine as claimed in claim 1 or 2, wherein $R_2$ and $R_4$ are each a benzylamino group of structural formulae II and $R_1$ and $R_3$ are selected from the group consisting of 2-methoxyethoxy, propoxy, 2-hydroxypropoxy, diethanolamino, solketalo, 2-hydroxyethoxy and 3-hydroxypropoxy.

5. A pyrimidopyrimidine as claimed in claim 1 or 2, wherein $R_2$ and $R_4$ are each a benzylamino group of formula II in which at least one of $R_6$ and $R_7$ is alkoxy.

6. A pyrimidopyrimidine as claimed in claim 5, wherein $R_6$ is selected from 4-methoxy and 3-methoxy substituents.

7. A pyrimidopyrimidine as claimed in claim 5, wherein $R_5$ is methyl.

8. A pyrimidopyrimidine as claimed in claim 1 or 2 wherein $R_2$ and $R_4$ are each a benzylamino group conforming to structural formulae II in which the combination of substituents $R_5$, $R_6$ and $P_7$ is selected from the following combinations:

| $R_5$ | $R_6$ | $R_7$ |
|---|---|---|
| H | 4-OMe | H |
| Me | 4-OMe | H |
| H | 4-OMe | 3-OMe |
| Me | 4-OMe | 3-OMe |
| H | H | H |
| Me | H | H |
| benzyl | H | H |
| H | 4-$CF_3$ | H |

9. A pyrimidopyrimidine compound which is one of the following:

2,6-di-(3-hydroxypropoxy)-4,8-di-(N 4-methoxybenzyl-N-methylamino)pyrimidopyrimidine;

2,6-bis-diethanolamino-4,8-di-(4-methoxybenzylamino) pyrimidopyrimidine;

2,6-bis-diethanolamino-4,8-bis-(3,4-dimethoxybenzylamino)pyrimidopyrimidine;

2,6-di-(2-hydroxypropoxy)-4,8-di-(4-methoxybenzylamino)pyrimidopyrimidine;

2,6-di(-3-hydroxypropoxy)-4,8-di(-4-methoxybenzylamino)pyrimidopyrimidine;

2,6-di-(2-hydroxyethoxy)-4,8-di-(N-4-methoxybenzyl-N-methylamino)pyrimidopyrimidine;

2,6-di(-3-hydroxypropoxy)-4,8-bis[(-3,4-dimethoxybenzyl)-N-methylamino] pyrimidopyrimidine;

2,6-bis(diethanolamino)-4,8-di(4-chlorobenzylamino) pyrimidopyrimidine;

2,6-di-(3-hydroxypropoxy)-4,8-di-(N-benzylmethylamino)pyrimidopyrimidine;

2,6-di(-2-hydroxyethoxy)-4,8-di(N-methylbenzylamino) pyrimidopyrimidine;

2,6-di-(-2-methoxyethoxy)-4,8-dibenzylaminopyrimidopyrimidine;

2,6-di-(2-methoxyethoxy)-4,8-di-(N-benzyl-N-methylamino)pyrimidopyrimidine;

2,6-disolketalo-4,8-dibenzylaminopyrimidopyrimidine;

2,6-bis-diethanolamino-4,8-di-(4-trifluoromethylbenzylamino)pyrimidopyrimidine;

2,6-di(-2-methoxyethoxy)-4,8-bis(dibenzylamino) pyrimidopyrimidine;

2,6-dipropoxy-4,8-di-(N-benzyl-N-methylamino) pyrimidopyrimidine;

2,6-di(-2-hydroxyethyl)amino-4,8-di(4-methoxybenzyl) aminopyrimidopyrimidine;

2,6-di(-2-hydroxyethylamino)-4,8-dibenzylaminopyrimidopyrimidine;

2,6-bis-diethanolamino-4,8-di-(N-methyl-N-[4-methoxybenzyl])aminopyrimidopyrimidine;

2,6-di-(2-hydroxyethyl)amino-4,8-bis-(3,4-dimethoxybenzyl)aminopyrimidopyrimidine;

2,6-Di-(3-hydroxypropoxy)-4,8-di-(N-[4-methoxybenzyl]-N-methyl)aminopyrimidopyrimidine;

2,6-Di-(2-hydroxyethoxy)-4,8-di-(N-benzyl-N-methyl) aminopyrimidopyrimidine.

10. A pyrimidopyrimidine compound as claimed in claim 1 said compound being in the form of an acid addition salt derived from an acid selected from the group consisting of:
hydrochloric, hydrobromic, sulphuric, nitric, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic.

11. A pharmaceutical composition containing a pyrimidopyrimidine compound as claimed in claim 1 and a pharmaceutically acceptable carrier thereof in unit dosage form.

12. A pharmaceutical composition comprising an effective cell membrane nucleoside or purine transport-inhibiting amount of a pyrimidopyrimidine compound as claimed in 1 or claim 9 admixed with a pharmaceutically acceptable carrier.

13. A pharmaceutical composition containing an effective amount of a pyrimidopyrimidine compound as claimed in claim 11 in admixture with a therapeutically effective amount of a cytotoxic drug for use in antitumour treatment.

14. A pharmaceutical composition containing as an active nucleoside transport inhibiting substance a pyrimidopyrimidine compound as claimed in claim 1 or claim 9 in admixture with a pharmaceutically acceptable carrier, diluent or excipient.

15. A method of inhibiting nucleoside or purine cell membrane transport, in a mammal said method comprising administering to said mammal an effective nucleoside or purine membrane transport-inhibiting amount of a compound having the formula I

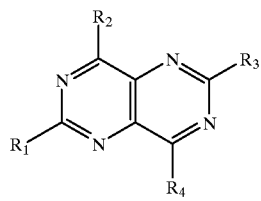

I or a pharmaceutically acceptable salt thereof,
characterised in that in structural formula I $R_1$ and $R_3$ are identical and are selected from allyl, diethanolamino, solketalo and a group having the formula —O—$R_Z$ or —NHR$_z$, $R_Z$ being selected from alkyl, hydroxyalkyl, alkoxyalkyl, dialkoxyalkyl and 2-oxo-alkyl wherein the or each alkyl and/or alkoxy moiety has less than six carbon atoms, and $R_2$ and $R_4$ are identical and are selected from N-tetrahydroisoquinolyl, and a benzylamino group having the structural formula II

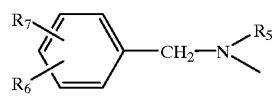

II where
$R_5$ is H, or optionally substituted alkyl or benzyl group, and
$R_6$ and $R_7$ represent H or optional substituents in the aromatic nucleus selected from halo, alkyl, alkoxy, hydroxy, trifluoromethyl, azido, cyano, nitro, carboxyl, carboxylic ester, amino or a substituted amino $NR_xR_y$ where $R_x$ and $R_y$ each represent hydrogen or alkyl,
subject to the proviso that
if $R_1$ and $R_3$ are both diethanolamino, $R_2$ and $R_4$ do not correspond to structure II with $R_5$, $R_6$ and $R_7$ each being hydrogen.

16. A method as claimed in claim 15 carried out in conjunction with administration of an antifolate cytotoxic drug in the course of antitumour therapy.

17. The method of claim 15 herein the compound is one selected from the group consisting of:
2,6-di-(3-hydroxypropoxy)-4,8-di-(N 4-methoxybenzyl-N-methylamino)pyrimidopyrimidine;
2,6-bis-diethanolamino-4,8-di-(4-methoxybenzylamino) pyrimidopyrimidine;
2,6-bis-diethanolamino-4,8-bis-(3,4-dimethoxybenzylamino)pyrimidopyrimidine;
2,6-di-(2-hydroxypropoxy)-4,8-di-(4-methoxybenzylamino)pyrimidopyrimidine;
2,6-di(-3-hydroxypropoxy)-4,8-di(-4-methoxybenzylamino)pyrimidopyrimidine;
2,6-di-(2-hydroxyethoxy)-4,8-di-(N-4-methoxybenzyl-N-methylamino)pyrimidopyrimidine;
2,6-di (-3-hydroxypropoxy)-4,8-bis[(-3,4-dimethoxybenzyl)-N-methylamino] pyrimidopyrimidine;
2,6-bis(diethanolamino)-4,8-di(4-chlorobenzylamino) pyrimidopyrimidine;
2,6-di-(3-hydroxypropoxy)-4,8-di-(N-benzylmethylamino)pyrimidopyrimidine;
2,6-di(-2-hydroxyethoxy)-4,8-di (N-methylbenzylamino)pyrimidopyrimidine;
2,6-di(-2-methoxyethoxy)-4,8-dibenzylaminopyrimidopyrimidine;
2,6-di-(2-methoxyethoxy)-4,8-di-(N-benzyl-N-methylamino)pyrimidopyrimidine;
2,6-disolketalo-4,8-dibenzylaminopyrimidopyrimidine;
2,6-bis-diethanolamino-4,8-di-(4-trifluoromethylbenzylamino)pyrimidopyrimidine;
2,6-di(-2-methoxyethoxy)-4,8-bis(dibenzylamino) pyrimidopyrimidine;
2,6-dipropoxy-4,8-di-(N-benzyl-N-methylamino) pyrimidopyrimidine;
2,6-di(-2-hydroxyethyl)amino-4,8-di(4-methoxybenzyl) aminopyrimidopyrimidine
2,6-di(-2-hydroxyethylamino)-4,8-dibenzylaminopyrimidopyrimidine
2,6-bis-diethanolamino-4,8-di-(N-methyl-N-[4-methoxybenzyl])aminopyrimidopyrimidine
2,6-di-(2-hydroxyethyl)amino-4,8-bis-(3,4-dimethoxybenzyl)aminopyrimidopyrimidine
2,6-Di-(3-hydroxypropoxy)-4,8-di-(N-[4-methoxybenzyl]-N-methyl) aminopyrimidopyrimidine
2,6-Di-(2-hydroxyethoxy)-4,8-di-(N-benzyl-N-methyl) aminopyrimidopyrimidine.

18. The method of increasing the cytotoxic effectiveness of a cytotoxic drug which comprises administering the drug together with an effective amount of a compound according to claim 1.

* * * * *